(12) United States Patent
Makriyannis et al.

(10) Patent No.: US 7,446,229 B2
(45) Date of Patent: *Nov. 4, 2008

(54) BICYCLIC CANNABINOIDS

(75) Inventors: Alexandros Makriyannis, Watertown, MA (US); Spyridon P. Nikas, Waltham, MA (US); Atmaram D. Khanolkar, Coventry, RI (US); Ganeshsingh A. Thakur, Waltham, MA (US); Dai Lu, Boston, MA (US)

(73) Assignee: University of Connecticut, Farmington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/609,580

(22) Filed: Dec. 12, 2006

(65) Prior Publication Data

US 2007/0135388 A1   Jun. 14, 2007

Related U.S. Application Data

(63) Continuation-in-part of application No. 11/344,762, filed on Jan. 31, 2006, now Pat. No. 7,285,683, which is a continuation of application No. 10/483,482, filed as application No. PCT/US02/21961 on Jul. 11, 2002, now Pat. No. 7,057,076.

(60) Provisional application No. 60/305,228, filed on Jul. 13, 2001.

(51) Int. Cl.
*C07C 49/115* (2006.01)
*C07C 49/23* (2006.01)
*C07D 311/78* (2006.01)
*A61K 31/35* (2006.01)

(52) U.S. Cl. .................. 568/326; 568/330; 549/280; 514/453

(58) Field of Classification Search .................. None
See application file for complete search history.

(56) References Cited

U.S. PATENT DOCUMENTS

| 6,943,266 B1 * | 9/2005 | Makriyannis et al. | 560/249 |
| 7,057,076 B2 * | 6/2006 | Makriyannis et al. | 568/326 |
| 7,285,683 B2 * | 10/2007 | Makriyannis et al. | 568/326 |

* cited by examiner

*Primary Examiner*—Sikarl A Witherspoon
(74) *Attorney, Agent, or Firm*—Alix, Yale & Ristas, LLP

(57) ABSTRACT

Bicyclic-cannabinoids and methods of preparation and use are presented. These compounds, when administered in a therapeutically effective amount to an individual or animal, results in a sufficiently high level of that compound in the individual or animal to cause a physiological response. The physiological response may be useful to treat a number of physiological conditions.

16 Claims, No Drawings

BICYCLIC CANNABINOIDS

CROSS REFERENCE TO RELATED APPLICATIONS

The present application is a continuation-in-part of U.S. patent application Ser. No. 11/344,762, filed Jan. 31, 2006, which is a continuation of U.S. patent application Ser. No. 10/483,482, filed Jan. 12, 2004, (now U.S. Pat. No. 7,057,076) which is the U.S. National Phase of International Application No. PCT/US02/21961, filed Jul. 11, 2002, which claims the benefit of United States Provisional Application No. 60/305,228, filed Jul. 13, 2001, the contents of each of which are incorporated herein by reference in their entirety.

FIELD

The present disclosure relates generally to cannabimimetic compounds. The disclosure is more particularly concerned with new and improved bicyclic cannabinoids exhibiting high binding affinities for at least one cannabinoid receptor, pharmaceutical preparations employing at least one of these compounds and methods of administering therapeutically effective amounts of at least one of these compounds to provide a physiological effect.

BACKGROUND

The classical cannabinoid $\Delta^9$-Tetrahydrocannabinol ($\Delta^9$-THC) is the major active constituent extracted from *Cannabis sativa*. The effects of cannabinoids are due to an interaction with specific high-affinity receptors. Presently, two cannabinoid receptors have been characterized: CB1, a central receptor found in the mammalian brain and a number of other sites in the peripheral tissues and CB2, a peripheral receptor found principally in cells related to the immune system. The CB1 receptor is believed to mediate the psychoactive properties, associated with classical cannabinoids. Characterization of these receptors has been made possible by the development of specific synthetic ligands such as the agonists WIN 55212-2 and CP 55,940.

In addition to acting at the cannabinoid receptors, cannabinoids such as $\Delta^9$-THC also affect cellular membranes, thereby producing undesirable side effects such as drowsiness, impairment of monoamine oxidase function and impairment of non-receptor mediated brain function. The addictive and psychotropic properties of some cannabinoids also limit their therapeutic value.

SUMMARY

Briefly stated, one aspect comprises novel bicyclic-cannabinoid compounds and their physiologically acceptable salts. The disclosed compounds include both the (−) and (+) enantiomers and all isomers. Some embodiments of this aspect are represented by the following compound formula 1.

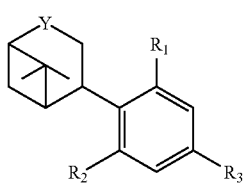

I

An advantageous variation of compound formula I is represented by compound formula Ia:

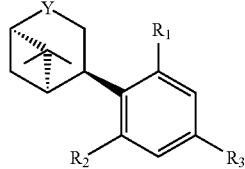

Ia

In one variation of compound formula Ia Y is selected from >C=O, >CH—(CH$_2$)$_f$—Y$_1$—(CH$_2$)$_g$—Y$_2$, >C=N—Y$_3$, >CH—NY$_4$Y$_5$, >CH—(CH$_2$)$_h$—Y$_6$ or >C=CY$_7$Y$_8$, including all isomers.

Y$_1$ is independently selected from O, CO, C(O)O, OC(O) or CH$_2$.

Y$_2$ is independently selected from H, halogen, CN, CF$_3$, N$_3$, OH, NH$_2$, COOH, alkoxy, acyloxy, NCS or NCO.

Y$_3$ is independently selected from —OH, —NH$_2$, alkoxy, alkyl, —(CH$_2$)$_n$—NR$_{10}$R$_{11}$, —(CH$_2$)$_n$—CO$_2$R (where R comprises H or alkyl), —O—(CH$_2$)$_n$—NR$_{10}$R$_{11}$, —O—(CH$_2$)$_n$—CO$_2$R (where R comprises H or alkyl) or —O—(CH$_2$)$_n$—CONR$_{10}$R$_{11}$.

Y$_4$ is independently selected from H, OH, alkoxy or alkyl.

Y$_5$ is independently selected from H, OH, alkoxy or alkyl, wherein Y$_4$ and Y$_5$ cannot both be OH and wherein Y$_4$ and Y$_5$ cannot both be alkoxy.

Y$_6$ is independently selected from H, halogen, CN, COOH, NH$_2$, SO$_2$Cl, SO$_2$F, SO$_3$H, COalkyl, CF$_3$, SO$_2$alkyl, COfluoroalkyl, N$_3$, OH, alkoxy, acyloxy, NCS or NCO.

Y$_7$ and Y$_8$ are each independently selected from H, alkyl, alkenyl, CN, OH, alkoxy or —(CH$_2$)$_n$—NR$_{10}$R$_{11}$.

R$_{10}$ and R$_{11}$ are each independently selected from H, alkyl, hydroxyalkyl, or R$_{10}$ and R$_{11}$ together comprise part of a 3 to 7 membered saturated heterocyclic ring containing up to one additional heteroatom selected from N, O and S.

f is an integer from 0 to about 5.
g is an integer from 0 to about 5.
h is an integer from 0 to about 5.
n is an integer from 0 to about 4.

As used in this disclosure when an integer such as f, g, h or n is 0 the structural portion modified by that integer is absent and the adjacent subunits are directly connected. For example, >CH—(CH$_2$)$_h$—Y$_6$, where h is 0 means that the (CH$_2$)$_0$ portion is absent so that the >CH and —Y$_6$ subunits are directly connected to provide the moiety >CH—Y$_6$.

R$_1$ and R$_2$ are each independently selected from H, OH, NH$_2$, NO$_2$, CN, OCOCH$_3$, OC(O)CH=CHCOOH, halogen, alkyl, —O-alkyl, acyl, aroyl, benzoyl, substituted benzoyl, phenacyl, substituted phenacyl, —O-alkyl-aryl, —O-alkyl-NR$_{10}$R$_{11}$, —O-alkyl-COOR (where R is selected from H or alkyl), —O-alkyl-CONR$_{10}$R$_{11}$, —N(alkyl)$_2$, —CO(alkyl)X or —OCO(alkyl)X or OCO(alkenyl)X (where X is selected from H, COOH, dialkylamino, a cyclic amine, a carbocyclic ring, a heterocyclic ring, an aromatic ring or a heteroaromatic ring), —O—P(O)(OR)$_2$ or —O—P(O)(OH)(OR) (where R is selected from H or alkyl), —P(O)(OR)$_2$ (where R is selected from H or alkyl), —P(O)(OH)(OR) (where R is selected from H or alkyl) or —OC(O)—CH(NH$_2$)—R$_{16}$ (where R$_{16}$ is selected from H, CH(OH)CH$_3$ or alkyl-X$_3$ and X$_3$ is selected from: H, —NH—C(=NH)NH$_2$, C(O)NH$_2$, COOH, SH, SCH$_3$, OH, NH$_2$, a substituted or unsubstituted aromatic ring, a substituted or unsubstituted heteroaromatic ring, a substituted or unsubstituted heterocyclic ring.

$R_{10}$ and $R_{11}$ are each independently selected from H, alkyl, hydroxyalkyl or $R_{10}$ and $R_{11}$ together comprise part of a 3 to 7 membered saturated heterocyclic ring containing up to one additional heteroatom selected from N, O and S.

$R_3$ is selected from the following structures:

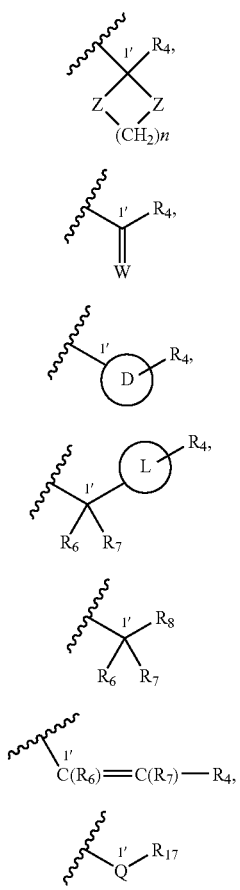

wherein each Z is independently selected from S, O NH, N(CH$_3$), SO, SO$_2$, or CR$_{12}$R$_{13}$ where $R_{12}$ and $R_{13}$ are each independently selected from H or alkyl.

W is selected from O, S or CR$_{12}$R$_{13}$ where $R_{12}$ and $R_{13}$ are each independently selected from H or alkyl.

D is selected from a cycloalkyl ring, a heterocyclic ring, an adamantyl ring, an heteroadamantyl ring or any above ring optionally substituted by $R_4$ in any possible position with the proviso that ring D can not be bonded to $R_4$ from the 1' position.

L is selected from a cycloalkyl ring, a heterocyclic ring, an aromatic ring, a heteroaromatic ring, an adamantyl ring, an heteroadamantyl ring or any above ring optionally substituted by $R_4$ in any possible position.

$R_4$ is selected from —(CH$_2$)$_j$—R$_5$, —(CH$_2$)$_j$-A-(CH$_2$)$_k$—R$_5$ or —(CH$_2$)$_j$-A-(CH$_2$)$_k$—B—R$_5$.

A and B are each independently selected from —CH$_2$—CH$_2$—, —CH=CH—, —C≡C—, O, S, SO, SO$_2$ or NH.

$R_5$ is selected from H, halogen, CN, CF$_3$, N$_3$, COOH, NH$_2$, N(CH$_3$)$_2$, ⊕N(CH$_3$)$_3$, Sn(alkyl)$_3$, phenyl, OH, NCS, NCO, NO$_2$, CHO, SO$_3$H, SO$_2$Cl, SO$_2$F, PO$_3$H$_2$, C(O)CF$_3$, SH, —CH=CH$_2$, —C≡CH, NH(alkyl), N(alkyl)$_2$, O-aryl, alkoxy, thioalkoxy, sulfonamide, COOR (where R is selected from H or alkyl), a substituted or unsubstituted carbocylic ring, a substituted or unsubstituted heterocyclic ring, a substituted or unsubstituted aromatic ring, a substituted or unsubstituted heteroaromatic ring, a polycarbocyclic ring structure having 2 to about 5 rings, a polyheterocyclic ring structure having 2 to about 5 rings or CONR$_{10}$R$_{11}$ (where $R_{10}$ and $R_{11}$ are each independently selected from H, alkyl, hydroxyalkyl, or $R_{10}$ and $R_{11}$ together comprise part of a 5 or 6 membered saturated heterocyclic ring containing up to one additional heteroatom selected from N, O and S).

n is an integer from 0 to about 4.
j is an integer from 0 to about 7.
k is an integer from 0 to about 7.

As noted above when an integer such as n, j or k is 0 the structural portion modified by that integer is absent and the adjacent subunits are directly connected. For example, when n is 0 structure Ia 1 comprises a 3 member ring.

$R_6$ and $R_7$ are each independently selected from H or alkyl.
$R_8$ is selected from —(CH$_2$)$_j$—C≡C—(CH$_2$)$_k$—R$_5$ or —(CH$_2$)$_j$—C(R$_6$)=C(R$_7$)—(CH$_2$)$_k$—R$_5$ where $R_5$, $R_6$ and $R_7$ are as previously defined.

j is an integer from 0 to about 7.
k is an integer from 0 to about 7.

As noted above when an integer is 0 the structural portion modified by that integer is absent and the adjacent subunits are directly connected.

Q is selected from O, S, NH or N(R$_{18}$) (where $R_{18}$ is selected from SO$_2$-aryl, alkyl-R$_5$, aryl-R$_5$ or heteroaryl-R$_5$).

$R_{17}$ is selected from alkyl-R$_5$, aryl-R$_5$ or heteroaryl-R$_5$.

In another variation of compound formula Ia Y is >CH—(CH$_2$)$_h$—Y$_6$.

$Y_6$ is CN and h is an integer from about 1 to about 3, or
$Y_6$ is selected from I, N$_3$, SO$_2$Cl, SO$_2$F, SO$_3$H, COOH, COalkyl, CF$_3$, SO$_2$alkyl, COfluoroalkyl, OH, alkoxy, acyloxy, NCS, NCO or NH$_2$, and h is an integer from 0 to about 3.

$R_1$ and $R_2$ are each independently as previously defined.
$R_3$ is:

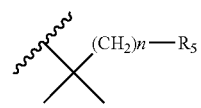

where $R_5$ is as previously defined and n comprises an integer from 0 to about 7 where n=0 means that the linking carbon chain is absent and the dimethyl and $R_5$ subunits are directly connected.

In another variation of compound formula Ia Y is selected from >C=O or >C=CY$_7$Y$_8$, including all isomers, where $Y_7$ and $Y_8$ are each independently as previously defined.

$R_1$ and $R_2$ are each independently as previously defined.
$R_3$ is:

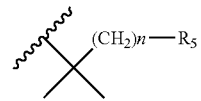

where $R_5$ is as previously defined and n comprises an integer from 0 to about 7. When n is 0 the linking carbon chain is absent and the dimethyl and $R_5$ subunits are directly connected.

The following provisos can apply to the compounds of formula Ia.

If Y is C=O, and $R_1$ is selected from H, OH, $OCH_3$, $NH_2$, $O(CH_2)_nN(CH_3)_2$ (where n is an integer from 1-3) or

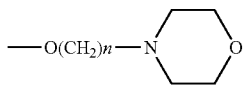

(where n is an integer between 1-3), and $R_2$ is selected from H, OH or $OCH_3$, then $R_3$ cannot be selected from $(CH_2)_nC$≡$CH$ where n is an integer from 3-5 or

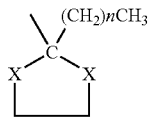

where each X is independently selected from $CH_2$, O, S and NH and n is an integer from 3-5.

If Y is C=O, and $R_1$ is selected from H, OH, $OCH_3$, $NH_2$, $O(CH_2)_nN(CH_3)_2$ (where n is an integer from 1-3) or

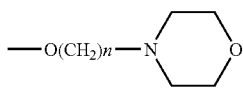

(where n is an integer between 1-3), and $R_2$ is selected from H, OH or $OCH_3$, then $R_3$ cannot be selected from structure Ia 3 where D is an adamantyl ring and $R_4$ is selected from H, $(CH_2)_nCH_3$ (where n is an integer from 4-6) or $C(CH_3)_2(CH_2)_n CH_3$ (where n is an integer from 3-5).

If Y is C=O, and $R_1$ and $R_2$ are both OH, then $R_3$ cannot be $C(CH_3)_2(CH_2)_nCH_3$ (where n is an integer from 3-5).

If Y is C=O, and $R_1$ and $R_2$ are both OH, then $R_3$ cannot be structure Ia 3, where D is a 5 to 8 membered unsubstituted cycloalkyl ring or 5 to 8 membered unsubstituted cycloalkenyl ring and $R_4$ is H.

If Y is C=O, and $R_1$ and $R_2$ are both OH, then $R_3$ cannot be structure Ia 5, where $R_6$ and $R_7$ are both H and $R_8$ is $(CH_2)_j$—$C(R_6)$=$C(R_7)$—$(CH_2)_k$—$R_5$ where $R_5$ is H and the sum of j and k is equal to 4-9.

If Y is C=O, and $R_1$ and $R_2$ are both OH, then $R_3$ cannot be $CH$=$CH(CH_2)_nCH_3$ where n is an integer from 2-7.

In one advantageous variation of compound formula Ia Y is >C=O; $R_1$ and $R_2$ are each OH; and $R_3$ is selected from

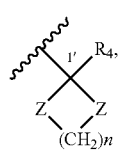 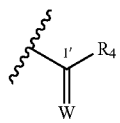 or 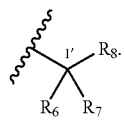

In one advantageous variation of compound formula Ia Y is >C=O; $R_1$ and $R_2$ are each OH; $R_3$ is

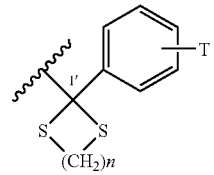

T is selected from alkyl, alkyl substituted with one or more groups selected from halogen, OH, CN, sulfonamide, NCS or $NO_2$; alkenyl, alkenyl substituted with one or more groups selected from halogen, OH, CN, sulfonamide, NCS or $NO_2$; alkynyl or alkynyl substituted with one or more groups selected from halogen, OH, CN, sulfonamide, NCS or $NO_2$; and n is an integer 0 to 3.

In one advantageous variation of compound formula Ia Y is >C=O; $R_1$ and $R_2$ are each OH; $R_3$ is

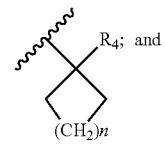

n is an integer 0 to 3.

In one advantageous variation of compound formula Ia Y is >C=O; $R_1$ and $R_2$ are each OH; $R_3$ is

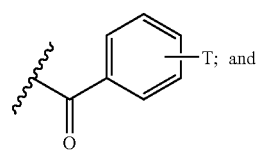

T is selected from alkyl, alkyl substituted with one or more groups selected from halogen, OH, CN, sulfonamide, NCS or $NO_2$; alkenyl, alkenyl substituted with one or more groups selected from halogen, OH, CN, sulfonamide, NCS or $NO_2$; alkynyl or alkynyl substituted with one or more groups selected from halogen, OH, CN, sulfonamide, NCS or $NO_2$.

Another advantageous variation of compound formula I is compound formula Ib:

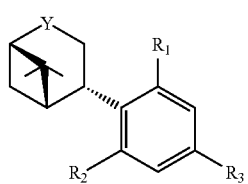

In one variation of compound formula Ib:
Y is selected from >C=O, >CH—$(CH_2)_f$—$Y_1$—$(CH_2)_g$—$Y_2$, >C=N—$Y_3$, >CH—$NY_4Y_5$ or >CH—$(CH_2)_h$—$Y_6$, including all isomers.

$Y_1$ is independently selected from O, C(O)O or $CH_2$.

$Y_2$ is independently selected from H, I, CN, $CF_3$, $N_3$, NCS or NCO.

$Y_3$ is independently selected from OH, $NH_2$, C1-C4 alkoxy, C1-C4 alkyl, —$(CH_2)_n$—$NR_{10}R_{11}$, —$(CH_2)_n$—$CO_2R$ (where R comprises H or alkyl), —O—$(CH_2)_n$—$NR_{10}R_{11}$, —O—$(CH_2)_n$—$CO_2R$ (where R comprises H or alkyl) or —O—$(CH_2)_n$—$CONR_{10}R_{11}$.

$Y_4$ is independently selected from H, OH, C1-C4 alkoxy or C1-C4 alkyl.

$Y_5$ is independently selected from H, OH, C1-C4 alkoxy or C1-C4 alkyl, wherein $Y_4$ and $Y_5$ cannot both be OH and wherein $Y_4$ and $Y_5$ cannot both be C1-C4 alkoxy.

$Y_6$ is independently selected from I, CN, $SO_2Cl$, $SO_2F$, COalkyl, $CF_3$, COfluoroalkyl, $N_3$, NCS or NCO.

$R_{10}$ and $R_{11}$ are each independently selected from hydroxyalkyl, or $R_{10}$ and $R_{11}$ together comprise part of a 3 to 7 membered saturated heterocyclic ring containing one additional heteroatom selected from N, O and S.

f comprises an integer from 0 to about 5.

g comprises an integer from 0 to about 5.

h comprises an integer from 0 to about 5.

n comprises an integer from 0 to about 4.

As noted above when an integer such as f, g, h or n is 0 the structural portion modified by that integer is absent and the adjacent subunits are directly connected. For example, >CH—$(CH_2)_h$—$Y_6$, where h is 0 means that the $(CH_2)_0$ portion is absent so that the >CH and —Y6 subunits are directly connected to provide the moiety >CH—$Y_6$.

$R_1$ and $R_2$ are each independently selected from OH, $OCH_3$, $NO_2$, CN, $OCOCH_3$, aroyl, benzoyl, substituted benzoyl, phenacyl, substituted phenacyl, —O-alkyl-aryl, —O-alkyl-$NR_{10}R_{11}$, —O-alkyl-$CONR_{10}R_{11}$, —CO(alkyl)X or —OCO(alkyl)X (where X is selected from a cyclic amine, a carbocyclic ring, a heterocyclic ring, an aromatic ring or a heteroaromatic ring), —OC(O)—$CH(NH_2)$—R (where R comprises H or CH(OH)$CH_3$) or alkyl-X (where X is selected from H, —NH—C(=NH)$NH_2$, $C(O)NH_2$, COOH, SH, $SCH_3$, OH, $NH_2$, a substituted or unsubstituted aromatic ring, a substituted or unsubstituted heteroaromatic ring, a substituted or unsubstituted heterocyclic ring).

$R_{10}$ and $R_{11}$ are each independently selected from hydroxyalkyl, or $R_{10}$ and $R_{11}$ together comprise part of a 3 to 7 membered saturated heterocyclic ring containing one additional heteroatom selected from N, O and S.

$R_3$ is selected from the following structures:

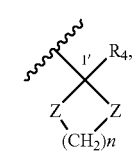
Ib 1

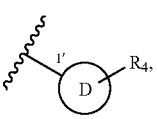
Ib 2

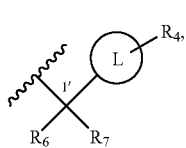
Ib 3

-continued

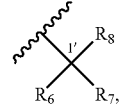
Ib 4

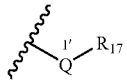
Ib 5 wherein each Z is independently selected from $CH_2$, S, O, NH, $N(CH_3)$, SO or $SO_2$.

D comprises a heterocyclic ring, an adamantyl ring, an heteroadamantyl ring or any above ring optionally substituted by $R_4$ in any possible position with the proviso that ring D can not be bonded to $R_4$ from the 1' position.

L comprises a cycloalkyl ring, a heterocyclic ring, a heteroaromatic ring, an adamantyl ring, a heteroadamantyl ring or any above ring optionally substituted by $R_4$ in any possible position.

$R_4$ is —$(CH_2)_j$—$(CH_2)_k$—$R_5$.

A is selected from —$CH_2$—$CH_2$—, —CH=CH—, —C≡C—, O, S, SO, $SO_2$ or NH.

$R_5$ is selected from H, halogen, CN, $CF_3$, $N_3$, COOH, $NH_2$, $N(CH_3)_2$, $\oplus N(CH_3)_3$, Sn(alkyl)$_3$, phenyl, pyrrolidine ring, piperidine ring, morpholine ring, cyclopropyl, cyclobutyl, cyclopentyl, cyclohexyl, cycloheptyl, NCS, NCO, $SO_3H$, $SO_2Cl$, $SO_2F$, $PO_3H_2$, $C(O)CF_3$, —O-aryl, sulfonamide, a carbocyclic ring, a heterocyclic ring, a heteroaromatic ring, a polycarbocyclic ring structure having 2 to about 5 rings, a polyheterocyclic ring structure having 2 to about 5 rings or $CONR_{10}R_{11}$ (where $R_{10}$ and $R_{11}$ are each independently selected from hydroxyalkyl, or $R_{10}$ and $R_{11}$ together comprise part of a 5 or 6 membered saturated heterocyclic ring containing one additional heteroatom selected from N, O and S).

n comprises an integer from 0 to about 3.

j comprises an integer from 0 to about 7.

k comprises an integer from 0 to about 7.

As noted above when an integer such as n, j or k is 0 the structural portion modified by that integer is absent and the adjacent subunits are directly connected. Thus, when n is 0 formula Ib 1 comprises a 3 member ring.

$R_6$ and $R_7$ are each independently selected from H or $CH_3$.

$R_8$ is selected from —$(CH_2)_j$—C≡C—$(CH_2)_k$—$R_5$ or —$(CH_2)_j$—CH=CH—$(CH_2)_k$—$R_5$ where $R_5$ is as defined above for formula Ib.

j comprises an integer from 0 to about 7.

k comprises an integer from 0 to about 7.

As noted above when an integer is 0 the structural portion modified by that integer is absent and the adjacent subunits are directly connected.

Q is selected from O, S, NH or $N(R_{18})$ (where $R_{18}$ is selected from $SO_2$-aryl, alkyl-$R_5$, aryl-$R_5$ or heteroaryl-$R_5$).

$R_{17}$ is selected from alkyl-$R_5$, aryl-$R_5$ or heteroaryl-$R_5$ with the proviso that $R_5$ cannot be hydrogen.

In another variation of compound formula Ib Y is >CH—$(CH_2)_h$—$Y_6$.

$Y_6$ is selected from CN and h is an integer from about 1 to about 3, or $Y_6$ is selected from $N_3$, $SO_2Cl$, $SO_2F$, COalkyl, $CF_3$, COfluoroalkyl, NCS or NCO and h is an integer from 0 to about 3.

$R_1$ and $R_2$ are each independently selected from OH or $OCH_3$.

$R_3$ is:

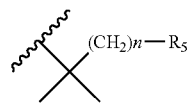

where $R_5$ is as defined above for formula Ib and n comprises an integer from 0 to about 7.

As noted above when an integer is 0 the structural portion modified by that integer is absent and the adjacent subunits are directly connected.

The following provisos can apply to the compounds of compound formula Ib.

If Y is C=O, and $R_1$ and $R_2$ are both OH, then $R_3$ cannot be $C(CH_3)_2(CH_2)_nCH_3$ (where n is an integer from 3-5).

If Y is C=O, and $R_1$ and $R_2$ are both OH, then $R_3$ cannot be structure Ib 4, where $R_6$ and $R_7$ are both H and $R_8$ is $(CH_2)_j$—CH=CH—$(CH_2)_k$—$R_5$ where $R_5$ is H and the sum of j and k is equal to 4-9.

Unless otherwise specifically defined, "acyl" refers to the general formula —C(O)alkyl.

Unless otherwise specifically defined, "acyloxy" refers to the general formula —O-acyl.

Unless otherwise specifically defined, "alcohol" refers to the general formula alkyl-OH.

Unless otherwise specifically defined, "alkenyl" or "lower alkenyl" refers to a linear, branched or cyclic carbon chain having from 1 to about 16 carbon atoms, and advantageously about 1 to about 6 carbon atoms, and at least one double bond between carbon atoms in the chain. Examples include, for example, ethylene, allene, butene, butadiene, hexene, hexadiene, 5,5-dimethyl-1-hexene and cyclohexene. Unless otherwise specifically limited an alkenyl group can be unsubstituted, singly substituted, or multiply substituted, with substituent groups in any possible position.

Unless otherwise specifically defined, "alkoxy" refers to the general formula —O-alkyl.

Unless otherwise specifically defined, "alkyl" refers to a linear, branched or cyclic alkyl group having from 1 to about 9 carbon atoms including, for example, methyl, ethyl, propyl, butyl, hexyl, octyl, isopropyl, isobutyl, tert-butyl, cyclopropyl, cyclohexyl, cyclooctyl, vinyl and allyl. Unless otherwise specifically defined, an alkyl group can be saturated or unsaturated and substituted or unsubstituted. Unless otherwise specifically limited, a cyclic alkyl group includes monocyclic, bicyclic and polycyclic rings, for example norbornyl, adamantyl and related terpenes.

Unless otherwise specifically defined, "alkylamino" refers to the general formula —(NH)-alkyl.

Unless otherwise specifically defined, "di-alkylamino" refers to the general formula —N-(alkyl)$_2$. Unless otherwise specifically limited di-alkylamino includes cyclic amine compounds such as piperidine and morpholine.

Unless otherwise specifically defined, "alkylmercapto" refers to the general formula —S-alkyl.

Unless otherwise specifically defined, "alkynyl" or "lower alkynyl" refers to a linear, branched or cyclic carbon chain having from 1 to about 16 carbon atoms, and advantageously about 1 to about 6 carbon atoms, and at least one triple bond between carbon atoms in the chain. Examples include, for example, ethyne, butyne, and hexyne. Unless otherwise specifically limited an alkynyl group can be unsubstituted, singly substituted, or multiply substituted, with substituent groups in any possible position.

Unless otherwise specifically defined, an aromatic ring is an unsaturated ring structure having about 5 to about 6 ring members and including only carbon as ring atoms. Unless otherwise specifically defined, an aromatic ring can be substituted or unsubstituted.

Unless otherwise specifically defined, "aryl" refers to an aromatic ring system substituted or unsubstituted, that includes only carbon as ring atoms, for example phenyl, biphenyl or napthyl.

Unless otherwise specifically defined, "aroyl" refers to the general formula —C(=O)-aryl.

Unless otherwise specifically defined, a carbocyclic ring is a ring structure having about 3 to about 8 ring members, substituted or unsubstituted, that includes only carbon as ring atoms, for example, benzene or cyclohexane.

Unless otherwise specifically defined, "halogen" refers to an atom selected from fluorine, chlorine, bromine and iodine.

Unless otherwise specifically defined, a heteroaromatic ring is an unsaturated ring structure having about 5 to about 8 ring members, substituted or unsubstituted, that has carbon atoms and one or more heteroatoms, including oxygen, nitrogen and/or sulfur, as ring atoms. Heteroaromatic rings (or groups) also include fused polycyclic systems in which one or more monocyclic aromatic ring or monocyclic heteroaromatic ring is fused to another heteroaromatic ring. Examples of heteroaromatic rings (or groups) include but are not limited to, furan, thiophene, pyrrole, oxazole, thiazole, isoxazole, pyrazole, imidazole, oxadiazole, triazole, tetrazole, pyridine, pyrimidine, pyrazine, purine, benzothiazole, benzimibazole, benzofurane, indole, quinoline, quinoxaline.

Unless otherwise specifically defined "heteroaryl" refers to an heteroaromatic ring.

Unless otherwise specifically defined, a heterocyclic ring is a saturated ring structure having about 3 to about 8 ring members, substituted or unsubstituted, that has carbon atoms and one or more heteroatoms, including oxygen, nitrogen and/or sulfur, as ring atoms. Examples of heterocyclic rings include but are not limited to oxetane, thietane, azetidine, diazetidine, tetrahydrofuran, thiolane, pyrrolidine, dioxolane, oxathiolane, imidazolidine, dioxane, piperidine, morpholine, piperazine, and their derivatives. Unless otherwise specifically limited a heterocyclic ring includes monocyclic, bicyclic and polycyclic rings, for example azaadamantyl and tropanyl.

Unless otherwise specifically defined, the term "phenacyl" refers to the general formula -phenyl-acyl.

Unless otherwise specifically defined, a spirocycle refers to a ring system wherein a single atom is the only common member of two rings. A spirocycle can comprise a saturated carbocyclic ring comprising about 3 to about 8 ring members, a heterocyclic ring comprising about 3 to about 8 ring atoms wherein up to about 3 ring atoms may be N, S, or O or a combination thereof.

Unless otherwise specifically limited the term substituted means substituted by at least one below described substituent group in any possible position or positions. Substituent groups for the above moieties useful in the disclosed compounds are those groups that do not significantly diminish the biological activity of the disclosed compound. Substituent groups that do not significantly diminish the biological activity of the disclosed compound include, for example, H, halogen, $N_3$, NCS, CN, $NO_2$, $NX_1X_2$, $OX_3$, $C(X_4)_3$, OAc, O-acyl, O-aroyl, NH-acyl, NH-aroyl, NHCOalkyl, CHO, $C(halogen)_3$, $COOX_4$, $SO_3H$, $PO_3H_2$, $SO_2NX_1X_2$, $CONX_1X_2$, $C(O)CF_3$, alkyl, alcohol, alkoxy, alkylmercapto, alkylamino, di-alkylamino, sulfonamide or thioalkoxy wherein $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members and $X_4$ comprises H, alkyl, loweralkylhydroxy, or alkyl-$NX_1X_2$. Unless otherwise specifically limited, a substituent group may be in any possible position or any possible positions if multiply substituted.

Unless otherwise specifically limited the compounds of the present disclosure may have unnatural ratios of atomic isotopes at one or more of their atoms. For example, the compounds may be radiolabeled with isotopes, such as tritium, carbon-14, carbon-11, iodine-123, iodine-125 or fluorine-18. The present disclosure encompasses all isotopic variations of the described compounds, whether radioactive or not.

In general, unless otherwise explicitly stated the disclosed materials may be alternately formulated to comprise, consist of, or consist essentially of, any appropriate components or moieties herein disclosed. The disclosed materials may additionally, or alternatively, be formulated so as to be devoid, or substantially free, of any components, materials, ingredients, adjuvants moieties or species used in the prior art compositions or that are otherwise not necessary to the achievement of the function and/or objective of the present disclosure.

When the word "about" is used herein it is meant that the amount or condition it modifies can vary some beyond the stated amount so long as the function and/or objective of the disclosure are realized. The skilled artisan understands that there is seldom time to fully explore the extent of any area and expects that the disclosed result might extend, at least somewhat, beyond one or more of the disclosed limits. Later, having the benefit of this disclosure and understanding the concept and embodiments disclosed herein, a person of ordinary skill can, without inventive effort, explore beyond the disclosed limits and, when embodiments are found to be without any unexpected characteristics, those embodiments are within the meaning of the term about as used herein.

Testing of some disclosed compounds for their affinities for the central (CB1) and peripheral (CB2) cannabinoid receptors, showed a high affinity for the two cannabinoid receptors. Thus, an aspect is use of at least one of the disclosed compounds, and physiologically acceptable salts thereof, to bind to a cannabinoid receptor.

Some of the disclosed compounds showed high selectivity for the CB2 receptor. These CB2 selective compounds are able to bind to and stimulate the CB2 receptor without affecting the central (CB1) receptor to the same degree. Therefore, an aspect is use of at least one of the disclosed compounds, and physiologically acceptable salts thereof, to preferentially bind to the CB2 receptor.

The bicyclic-cannabinoids described herein, and physiologically acceptable salts thereof, have high potential when administered in therapeutically effective amounts for providing a physiological effect useful to treat pain, central pain, peripheral pain, neuropathy, neurodegenerative diseases including multiple sclerosis, Parkinson's disease, Huntington's chorea, Alzheimer's disease; mental disorders such as schizophrenia and depression; to prevent or reduce endotoxic shock and hypotensive shock; to modulate appetite; to modulate the immune system; to reduce fertility; to prevent or reduce diseases associated with motor function such as Tourette's syndrome; to prevent or reduce inflammation; to provide neuroprotection, to suppress memory, to produce peripheral vasodilation; to treat epilepsy, glaucoma, nausea such as associated with cancer chemotherapy, AIDS wasting syndrome, cancer as well as other ailments in which cannabinoid system is implicated. Thus, an aspect is the administration of a therapeutically effective amount of a disclosed compound, or a physiologically acceptable salt thereof, to an individual or animal to provide a physiological effect.

DESCRIPTION OF SOME PREFERRED EMBODIMENTS

As used herein a "therapeutically effective amount" of a compound, can be the quantity of a compound which, when administered to an individual or animal, results in a discernible physiological effect in the individual or animal. The compounds described herein, and physiologically acceptable salts thereof, can have pharmacological properties when administered in therapeutically effective amounts for providing a physiological effect useful to treat a number of physiological conditions.

Typically, a "therapeutically effective amount" of a disclosed compound is believed to range from about 5 mg/day to about 1,000 mg/day. The specific dosage level of active ingredient will depend upon a number of factors, including, for example, biological activity of the particular preparation, age, body weight, sex and general health of the individual being treated.

As used herein, an "individual" refers to a human. An "animal" refers to, for example, veterinary animals, such as dogs, cats, horses and the like, and farm animals, such as cows, pigs and the like.

The disclosed compound can be administered by a variety of known methods, including, for example, orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The formulations can also comprise one or more of a physiologically acceptable excipient, vehicle and optional adjuvants, flavorings, colorants and preservatives. Suitable physiologically acceptable vehicles include, for example, saline, sterile water, Ringer's solution and isotonic sodium chloride solutions. In an aspect the disclosed compounds are generally represented by compound formula I and include physiologically acceptable salts thereof. In another advantageous aspect the disclosed compounds are generally represented by compound formula Ia and include physiologically acceptable salts thereof. In another aspect the disclosed compounds are generally represented by the compound formula Ib and include physiologically acceptable salts thereof.

Compound Formulas I, Ia, Ib.

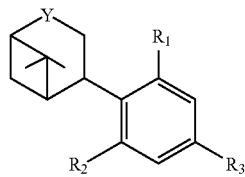

I

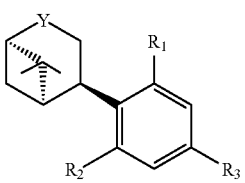

Ia

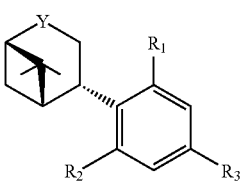

Ib

Some disclosed compounds were tested for CB2 receptor binding affinity and for CB1 receptor affinity (to determine selectivity). As used herein, "binding affinity" is represented by the $IC_{50}$ value or by the $K_i$ value, where $K_i$ as defined later and $IC_{50}$ is the concentration of a compound required to occupy the 50% of the total number (Bmax) of the receptors. The lower the $IC_{50}$ and/or $K_i$ value the higher the binding affinity. As used herein a compound is said to have "binding selectivity" if it has higher binding affinity for one receptor compared to the other receptor; e.g. a cannabinoid compound which has an $IC_{50}$ of 0.1 nM for CB1 and 10 nM for CB2, is 100 times more selective for the CB1 receptor. For the CB1 receptor binding studies, membranes were prepared from rat forebrain membranes according to the procedure of P. R. Dodd et al, *A Rapid Method for Preparing Synaptosomes: Comparison with Alternative Procedures*, Brain Res., 107-118 (1981). The binding of the novel analogues to the CB1 cannabinoid receptor was assessed as described in W. A. Devane et al, *Determination and Characterization of a Cannabinoid Receptor in a Rat Brain*, Mol. Pharmacol., 34, 605-613 (1988) and A. Charalambous et al, *5'-azido $\Delta^8$-THC: A Novel Photoaffinity Label for the Cannabinoid Receptor*, J. Med, Chem., 35, 3076-3079 (1992) with the following changes. The above articles are incorporated by reference herein.

Membranes, previously frozen at −80° C., were thawed on ice. To the stirred suspension was added three volumes of TME (25 mM Tris-HCl buffer, 5 mM $MgCl_2$ and 1 mM EDTA) at a pH 7.4. The suspension was incubated at 4° C. for 30 min. At the end of the incubation, the membranes were pelleted and washed three times with TME.

The treated membranes were subsequently used in the binding assay described below. Approximately 30 μg of membranes were incubated in silanized 96-well microtiter plate with TME containing 0.1% essentially fatty acid-free bovine serum albumin (BSA), 0.8 nM [$^3$H] CP-55,940, and various concentrations of test materials in a final volume of 200 μL. The assays were incubated for 1 hour at 30° C. and then immediately filtered using Packard Filtermate 196 harvester and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield $IC_{50}$ values. Data from at least two independent experiments performed in duplicate was used to calculate $IC_{50}$ values which were converted to $K_i$ values using the assumptions of Cheng et al, *Relationship Between the Inhibition Constant ($K_i$) and the concentration of Inhibitor which causes 50% Inhibition ($IC_{50}$) of an Enzymatic Reaction*, Biochem. Pharmacol., 22, 3099-3102, (1973), which is incorporated by reference herein.

For the CB2 receptor binding studies, membranes were prepared from frozen mouse spleen essentially according to the procedure of P. R. Dodd et al, *A Rapid Method for Preparing Synaptosomes: Comparison with Alternative Procedures*, Brain Res., 226, 107-118 (1981) which is incorporated by reference herein. Silanized centrifuge tubes were used throughout to minimize receptor loss due to adsorption. The CB2 binding assay was conducted in the same manner as for the CB1 binding assay. The binding affinities ($K_i$) were also expressed in nanomoles (nM). Some of the synthesized compounds disclosed below exhibited a high selectivity for the CB2 receptor (Tables 1a and 1b).

The following examples are given for purposes of illustration only in order that the present disclosure may be more fully understood. These examples are not intended to limit in any way the scope of the claims unless otherwise specifically indicated.

EXAMPLES

Synthesized bicyclic-cannabinoids of compound formula I are depicted in Tables 1a and 1b.

TABLE 1a
Table1a: Novel Bicyclic-cannabinoid compounds of compound formula Ia.
Ia
| Cmpd. number | Y Functionality | R₁ | R₂ | R₃ | CB1 Receptor Ki (nM) | CB2 Receptor Ki (nM) |
|---|---|---|---|---|---|---|
| 2.1 | 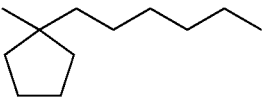 | OH | OH |  | 50.6 | 0.4 |
| 2.2 | 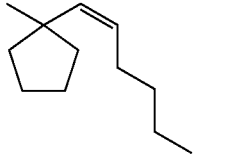 | OH | OH |  | 74.5 | 0.4 |
| 2.3 | 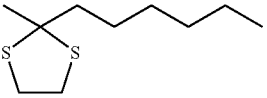 | OH | OH |  | 223.5 | 10.9 |
| 2.4 | 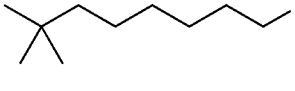 | OH | OH |  | 10.6 | 9.3 |
| 2.5 | 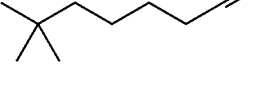 | OH | OH |  | 30.8 | 0.2 |
| 2.6 | 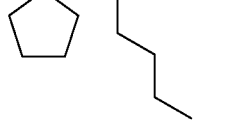 | OMe | OMe |  | 449 | 229 |
| 2.7 |  | OMe | OH |  | 453 | 53 |
| 2.8 | 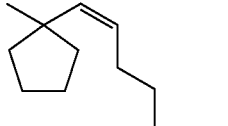 | OH | OH |  | 236 | 88 |
| 2.9 | 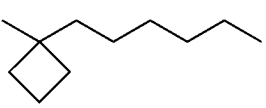 | OH | OH | | 97 | 6 |

TABLE 1a-continued
Table1a: Novel Bicyclic-cannabinoid compounds of compound formula Ia.
| Cmpd. number | Y Functionality | R₁ | R₂ | R₃ | CB1 Receptor Ki (nM) | CB2 Receptor Ki (nM) |
|---|---|---|---|---|---|---|
| 2.10 | 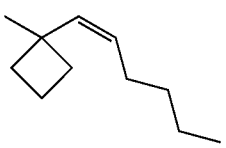 | OH | OH |  | 51.2 | 2.2 |
| 2.11 | 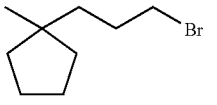 | OH | OH |  | 211 | 45 |
| 2.12 | 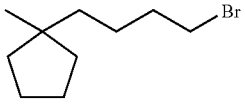 | OH | OH |  | 62.7 | 29.7 |
| 2.13 | 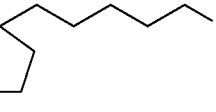 | OH | OH |  | 19.2 | 1.5 |
| 2.14 | 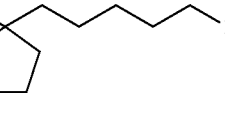 | OH | OH |  | 49.6 | 1.8 |
| 2.15 | 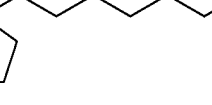 | OH | OH |  | 62.4 | 11.8 |
| 2.16 |  | OH | OH |  | 11.6 | 1.2 |
| 2.17 |  | OH | OH |  | 139 | 10.4 |
| 2.18 | 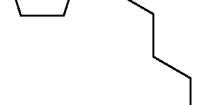 | OH | OH |  | 1464 | 45 |

TABLE 1a-continued
Table1a: Novel Bicyclic-cannabinoid compounds of compound formula Ia.
Ia
| Cmpd. number | Y Functionality | R$_1$ | R$_2$ | R$_3$ | CB1 Receptor Ki (nM) | CB2 Receptor Ki (nM) |
|---|---|---|---|---|---|---|
| 2.19 | 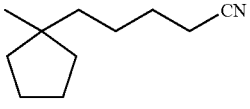 | OH | OH |  | 206 | 9.6 |
| 2.20 | 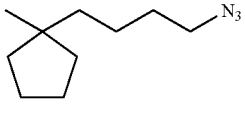 | OH | OH |  | 39.7 | 0.5 |
| 2.21 | 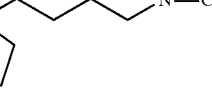 | OH | OH |  | 287 | 35.4 |
| 2.22 | 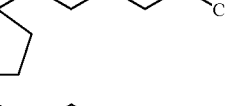 | OH | OH |  | 80.9 | 0.9 |
| 2.23 | 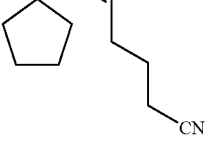 | OH | OH |  | 62.8 | 5.5 |
| 2.24 | 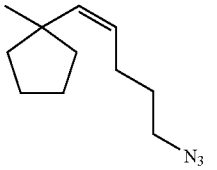 | OH | OH |  | 102 | 0.8 |
| 2.25 | 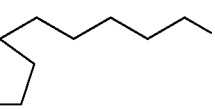 | OH | OH |  | 38.1 | 1.7 |
| 2.26 | 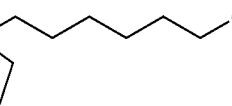 | OH | OH |  | 100 | 26.6 |
| 2.27 | 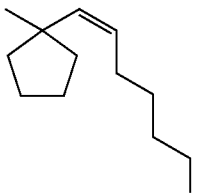 | OH | OH |  | 298 | 21.9 |

TABLE 1a-continued

Table1a: Novel Bicyclic-cannabinoid compounds of compound formula Ia.

Ia

| Cmpd. number | Y Functionality | $R_1$ | $R_2$ | $R_3$ | CB1 Receptor Ki (nM) | CB2 Receptor Ki (nM) |
|---|---|---|---|---|---|---|
| 2.28 | acetyl (C(=O)CH₃) | OH | OH | 1-(5-azidopentyl)cyclopentyl | 75.8 | 6.8 |
| 2.29 | acetyl | OH | OH | 2-methyloctan-2-yl | 82.1 | 13.5 |
| 2.30 | acetyl | OH | OH | 6-bromo-2-methylhexan-2-yl | 187 | 5.3 |
| 2.31 | acetyl | OH | OH | 7-bromo-2-methylheptan-2-yl | 76.7 | 5.0 |
| 2.32 | acetyl | OH | OH | 5-cyano-2-methylpentan-2-yl | 698 | 12.0 |
| 2.33 | acetyl | OH | OH | 6-cyano-2-methylhexan-2-yl | 62.2 | 12.9 |
| 2.34 | acetyl | OH | OH | 2-methyl-2-phenyl-1,3-dithiolane | 2980 | 32 |
| 2.35 | acetyl | OH | OH | phenacyl | 2045 | 22 |
| 2.36 | acetyl | OH | OH | 2-methyl-2-(4-methylphenyl)-1,3-dithiolane | 225 | 8.6 |

TABLE 1a-continued

Table1a: Novel Bicyclic-cannabinoid compounds of compound formula Ia.

| Cmpd. number | Y Functionality | $R_1$ | $R_2$ | $R_3$ | CB1 Receptor Ki (nM) | CB2 Receptor Ki (nM) |
|---|---|---|---|---|---|---|
| 2.37 | C=O (acetyl) | OH | OH | 4-acetylphenyl | 244 | 11.7 |
| 2.38 | C=O (acetyl) | OH | OH | 4-ethyl-(tert-butyl)phenyl | 951 | 122 |
| 2.39 | C=O (acetyl) | OH | OH | cyclohexyl-tert-butyl | 1212 | 274 |
| 2.40 | C=O (acetyl) | OH | OH | 2-methyl-2-(4-ethylphenyl)-1,3-dithiolane | 506 | 277 |
| 2.41 | C=O (acetyl) | OH | OH | 4-acetyl-ethylphenyl | 322 | 1153 |
| 2.42 | C=O (acetyl) | OH | OH | cumyl-phenyl | 688 | 122 |
| 2.43 | C=O (acetyl) | OH | OH | 4-methyl-(tert-butyl)phenyl | 707 | 185 |

TABLE 1a-continued
Table1a: Novel Bicyclic-cannabinoid compounds of compound formula Ia.
| Cmpd. number | Y Functionality | R₁ | R₂ | R₃ | CB1 Receptor Ki (nM) | CB2 Receptor Ki (nM) |
|---|---|---|---|---|---|---|
| 2.44 | 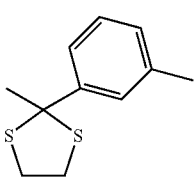 | OH | OH |  | 240 | 202 |
| 2.45 | 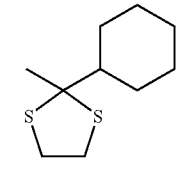 | OH | OH |  | 545 | 514 |
| 2.46 | 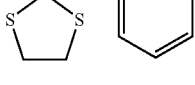 | OH | OH |  | 495 | 158 |
| 2.47 | 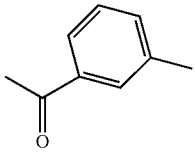 | OH | OH |  | — | — |
| 2.48 | 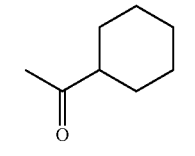 | OH | OH |  | 640 | 530 |
| 2.49 | 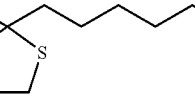 | OBn | OBn |  | 6933 | 10058 |
| 2.50 | 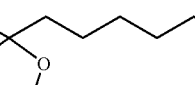 | OBn | OBn |  | 12351 | 17277 |
| 2.51 | 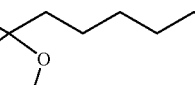 | OH | OH |  | 628 | 150 |
| 2.52 | 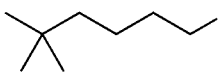 | OH | OH | 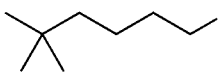 | 32.3 | 2.0 |

TABLE 1a-continued

Table1a: Novel Bicyclic-cannabinoid compounds of compound formula Ia.

Ia

| Cmpd. number | Y Functionality | R₁ | R₂ | R₃ | CB1 Receptor Ki (nM) | CB2 Receptor Ki (nM) |
|---|---|---|---|---|---|---|
| 2.53 | C=O (acetyl) | OH | OH | gem-dimethyl alkyl chain with N₃ | 30.7 | 2.7 |
| 2.54 | C=O (acetyl) | OH | OH | gem-dimethyl alkyl chain with N₃ | 9.1 | 5.7 |
| 2.55 | C=O (acetyl) | OH | OH | methyl adamantyl | 1892 | 59.3 |
| 2.56 | C=O (acetyl) | OH | OH | cyclopentyl dithiolane with methyl | — | — |
| 2.57 | C=O (acetyl) | OH | OH | N(Ts)-heptyl chain | 89.5 | 34.3 |
| 3. | CH—OH | OH | OH | hexyl dithiolane | 133.2 | 76.8 |

Ts is p-Toluenesulfonyl.
OBn is O—CH₂—Ph (where Ph is Phenyl).

TABLE 1b

Table 1b: Novel Bicyclic-cannabinoid compounds of formula Ib.

| Cmpd. number | Y Functionality | $R_1$ | $R_2$ | $R_3$ | CB1 Receptor Ki (nM) | CB2 Receptor Ki (nM) |
|---|---|---|---|---|---|---|
| 2.2e | \\=O (acetyl) | OH | OH | cyclopentyl-CH=CH-(CH2)3-CH3 | 69.2 | 0.7 |
| 2.14e | \\=O | OH | OH | cyclopentyl-(CH2)5-I | 5.0 | 0.5 |
| 2.22e | \\=O | OH | OH | cyclopentyl-(CH2)4-CN | 26.8 | 0.4 |
| 2.29e | \\=O | OH | OH | C(CH3)2-(CH2)5-CH3 | 18.2 | 1.2 |

Note that the "e" suffix indicates an enantiomer of a previously numbered compound. For example, compound 2.2e is the enantiomer of compound 2.2 in Table Ia.

Preparation of Compounds of Formula I, Ia, IIb

1. Resorcinol Synthesis

Resorcinol compounds 1.1 and 1.2 (shown in Scheme 1) were synthesized by a method depicted in Scheme 1, starting from (3,5-dimethoxyphenyl)cyclopentane carboxaldehyde, which was prepared by the method disclosed in Papahatjis D. P et al. *Chemistry Letters,* 192 (2001), and *J. Med. Chem.,* 46: 3221 (2003), the content of each of which are hereby incorporated by reference.

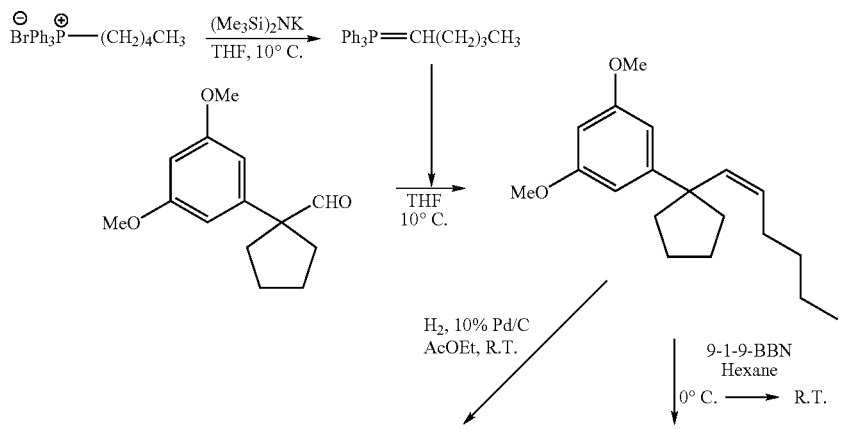

Scheme 1

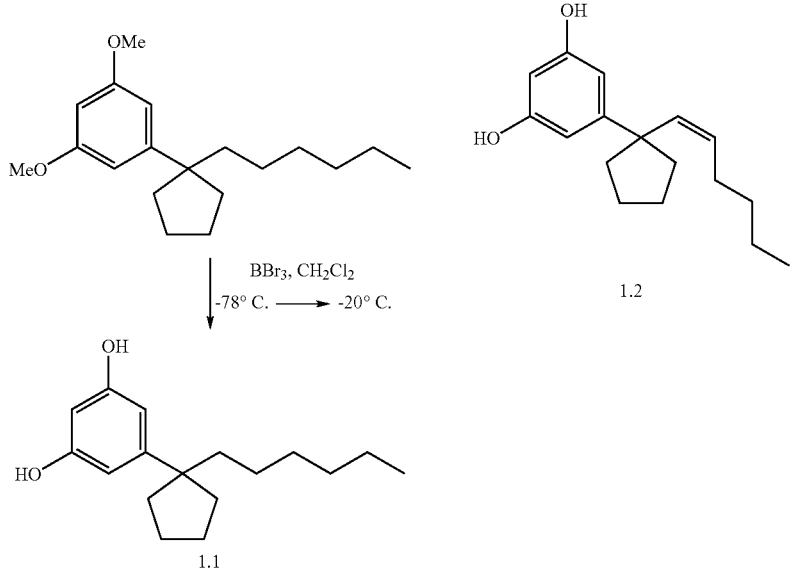

Procedure:

(Butylmethylene) triphenylphosphorane.

To a suspension of pentyltriphenylphosphonium bromide (5 equiv.) in dry THF (0.1 8M) at 0° C., under an argon atmosphere was added potassium bis(trimethylsilyl) amide (4.9 equiv.). The mixture was warmed to 10° C. and stirred for an additional 30 min to ensure complete formation of the orange ylide. The resulting slurry was used in the preparation of 1-(3,5-dimethoxyphenyl)-1-(hex-1-enyl)-cyclopentane.

1-(3,5-Dimethoxyphenyl)-1-(hex-1-enyl)-cyclopentane.

To the above slurry of (butylmethylene)triphenylphosphorane at 10° C. under an argon atmosphere was added dropwise a solution of (3,5-dimethoxyphenyl)cyclopentane carboxaldehyde (1 equiv.) in dry THF (0.21M). The reaction was stirred for 45 min and upon completion was quenched by the addition of saturated aqueous ammonium chloride. The organic layer was separated and the aqueous phase was extracted twice with diethyl ether. The combined organic layer was washed with brine, dried over MgSO$_4$ and the solvent was evaporated under reduced pressure to give an oil. The crude product was purified through a short column of silica gel using 5% diethyl ether-petroleum ether as eluent to afford the title compound in 96% yield.

1-(3,5-Dimethoxyphenyl)-1-hexyl-cyclopentane.

To a solution of 1-(3,5-dimethoxyphenyl)-1-(hex-1-enyl)-cyclopentane (1 equiv.) in ethyl acetate (0.11M) was added 10% Pd/C (17%, w/w) and the resulting suspension was stirred vigorously under an hydrogen atmosphere, overnight at room temperature. The catalyst was removed by filtration through celite and the filtrate was evaporated under reduced pressure to afford the crude product. Purification through a short column of silica gel using 5% diethyl ether-petroleum ether yielded the title compound in 95% yield.

5-(1-Hexyl-cyclopentyl)resorcinol, (compound 1.1).

To a solution of 1-(3,5-dimethoxyphenyl)-1-hexyl-cyclopentane (1 equiv.) in dry methylene chloride (0.04M) at −78° C. under an argon atmosphere was added boron tribromide (2.5 equiv., 1M solution in methylene chloride). Following the addition, the reaction temperature was gradually raised over a period of 3 h to −20° C. Stirring was continued at that temperature until completion of the reaction. Unreacted boron tribromide was destroyed by addition of methanol and ice at 0° C. The resulting mixture was warmed at room temperature, stirred for 40 min and the solvent was removed in vacuo. The residual oil was diluted with ethyl acetate and the solution was washed with saturated sodium bicarbonate, water and brine. The organic layer was dried over MgSO$_4$, filtered and concentrated under reduced pressure. Purification by flash column chromatography (40% diethyl ether-petroleum ether as eluent) afforded the title compound in 90% yield.

$^1$H NMR (500 MHz, CDCl$_3$) δ: 6.36 (d, J=1.6 Hz, 2H), 6.19 (t, J=1.6 Hz, 1H ), 5.78 (brs, 2H, OH ), 1.83-1.77 (m, 2H ), 1.73-1.58 (m, 6H ), 1.51-1.48 (m, 2H ), 1.22-1.12 (m, 6H ), 1.02-0.94 (m, 2H ), 0.83 (t, J=7.1 Hz, 3H).

5-[1-(Hex-1-enyl)-cyclopentyl]resorcinol, (Compound 1.2)

To a solution of 1-(3,5-dimethoxyphenyl)-1-(hex-1-enyl)-cyclopentane (1 equiv.) in dry hexane (0.05M) at 0° C. under an argon atmosphere was added 9-iodo-9-BBN (2.3 equiv., 1M solution in hexane). The mixture was stirred at the same temperature for 3.5 h and then the reaction temperature was raised to 27° C. Stirring was continued at that temperature until completion of the reaction. The volatiles were removed in vacuo, the residual oil was dissolved in diethyl ether, and a solution of ethanolamine (2.4 equiv.) in THF (1.4 M) was added causing spontaneous precipitation of the 9-BBN.ethanolamine adduct. The suspension was stirred for 2.5 h, the white precipitate was filtered off and the filtrate was evaporated under reduced pressure to give an oil. Purification by flash column chromatography on silica gel using 40% diethyl ether—petroleum ether as eluent afforded the title compound in 82% yield.

$^1$H NMR (500 MHz, CDCl$_3$) δ: 6.44 (d, J=1.9 Hz, 2H), 6.17 (t, J=1.9 Hz, 1H), 5.66 (d, J=11.0 Hz, 1H), 5.28(dt, J=11.0 Hz, J=7.3 Hz, 1H), 5.14(brs, 2H, OH), 2.01-1.85(m, 4H), 1.80-1.65(m, 6H), 1.15-1.07(m, 4H), 0.77(t, J=6.8 Hz, 3H).

Resorcinol compound 1.3 (shown in Scheme 3) was synthesized by the method disclosed in Papahatjis et al. *J. Med.*

Chem., 41: 1195 (1998), the content of which is hereby incorporated by reference. Resorcinol compounds 1.4, 1.30 and 1.31 (shown in Scheme 3) were synthesized by the method disclosed in Yan Guo et al. *J. Med. Chem.*, 37: 3867 (1994) and Nikas S. P et al. *AAPS Pharm Sci* 6(4), article 30 (2004), the contents of each of which are hereby incorporated by reference.

The hitherto unknown resorcinol compounds 1.9 and 1.10 (shown in Scheme 3) were synthesized starting from (3,5-dimethoxyphenyl)cyclobutane carboxaldehyde, and following the method described for the preparation of 1.1 and 1.2 (Scheme 1). (3,5-Dimethoxyphenyl)cyclobutane carboxaldehyde was in turn prepared by the method disclosed in Papahetjis D. P et al. *Chemistry Letters*, 192 (2001), the content of which is hereby incorporated by reference.

The hitherto unknown resorcinol compounds 1.11, 1.12, 1.13, 1.14, 1.15, 1.16 and 1.17 (shown in Scheme 3) were synthesized starting from the appropriate triphenylphosphonium salt and (3,5-dimethoxyphenyl)cyclopentane carboxaldehyde by following the method described for the preparation of 1.1 and 1.2 (Scheme 1). Thus, (2-phenoxyethyl)(triphenyl)phosphonium bromide has served as the starting point for the synthesis of 1.11, (3-phenoxypropyl)(triphenyl)phosphonium bromide has served as the starting point for the synthesis of 1.12, (4-phenoxybutyl)(triphenyl)phosphonium bromide has served as the starting point for the synthesis of 1.13, 1.14, 1.16, and (5-phenoxypentyl)(triphenyl)phosphonium bromide has served as the starting point for the synthesis of 1.15, 1.17.

Resorcinol compounds 1.34, 1.39, 1.42 and 1.45 (shown in Scheme 3) were synthesized by the method disclosed in Krishnamurthy et al. *Bioorg. Med. Chem. Lett.* 13: 3487 (2003), and in Nadipuram et al. *Bioorg. Med. Chem. Lett.* 11: 3121 (2003), the content of which is hereby incorporated by reference. The hitherto unknown resorcinol compounds 1.36, 1.38, 1.40, 1.43, 1.44, 1.46 and 1.56 (shown in Scheme 3) were synthesized by the same method.

Resorcinol compounds 1.5 and 1.57 (shown in Scheme 2) was synthesized by the methods depicted in Scheme 2.

Scheme 2

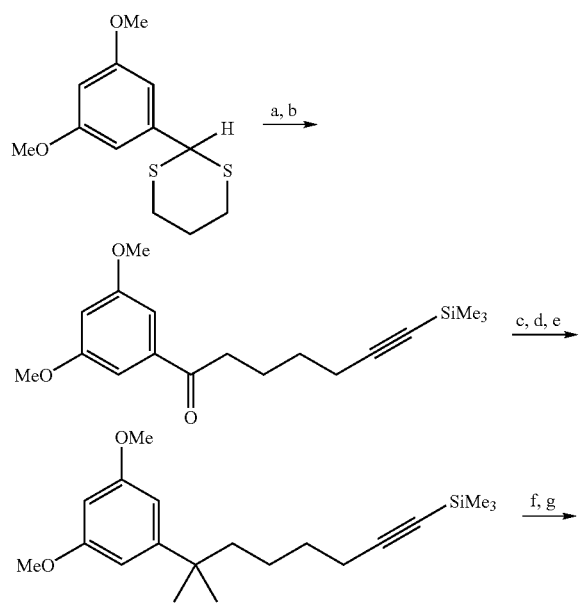

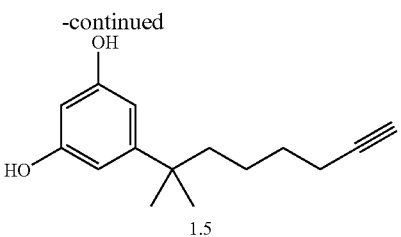

1.5

Reagents and conditions. a) n-BuLi, -30° C., THF, Br(CH$_2$)$_4$C≡CTMS; b) (CF$_3$COO)$_2$IPh, aq.MeOH; c) CH$_3$MgBr, Et$_2$O; d) HCl$_{(g)}$, CCl$_4$; e) Me$_3$Al, -30° C. to r.t. toluene; f) K$_2$CO$_3$, MeOH; g) BBr$_3$, -40° C. to 0° C. CH$_2$Cl$_2$.

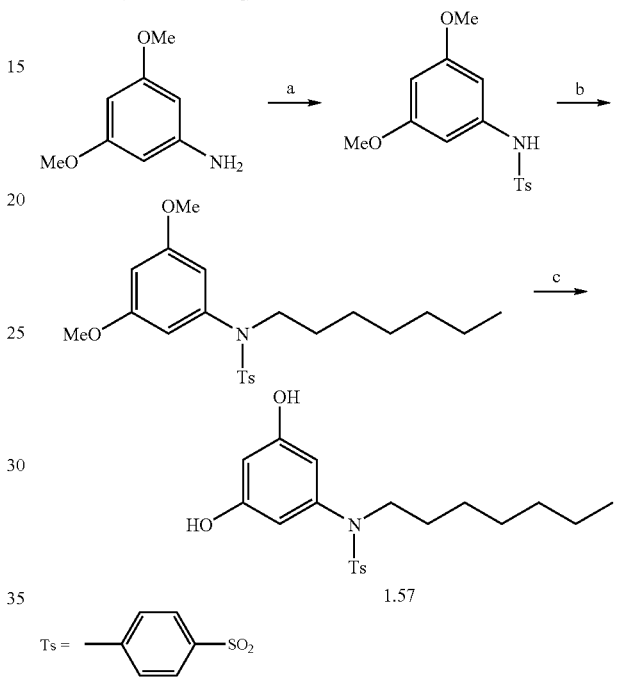

1.57

Ts = <structure: 4-methylphenyl-SO$_2$>

Reagents and conditions. a) TsCl, Pyridine, reflux, 30 min; b) CH$_3$(CH$_2$)$_6$Br, K$_2$CO$_3$, DMF, 120° C. 4h c) BCl$_3$, Bu$_4$NI, CH$_2$Cl$_2$, -78° C.-0° C., 2h.

Procedure for the Synthesis of Resorcinol Compound 1.5:

[7-(3,5-Dimethoxyphenyl-1,3-dithian-7-yl)-1-heptynyl]trimethylsilane.

A solution of 2-(3,5-dimethoxyphenyl)-1,3-dithiane (1 equiv.) in dry tetrahydrofuran (0.5 M) was cooled to -30° C. under argon and n-butyllithium (1.2 equiv., 1.6 M solution in hexanes) was added dropwise. The yellow-brown reaction mixture was stirred at the same temperature for 2 hours and (6-bromo-1-hexynyl)trimethylsilane (1.2 equiv.) was added in a dropwise manner when the color changed from yellow-brown to light yellow. The reaction mixture was allowed to warm to room temperature overnight and poured into water and extracted with diethyl ether. The combined organic extracts were dried and ether removed to give the crude product which was purified on silica gel (15% diethyl ether-petroleum ether) to afford the title compound in 86% yield as an oil.

Anal. calcd. for C$_{21}$H$_{32}$O$_2$S$_2$Si C, 61.72; H, 7.89; found C, 61.49; H, 8.24.

[7-(3,5-Dimethoxyphenyl)-7-oxo-1-heptynyl]trimethylsilane.

A solution of [7-(3,5-dimethoxyphenyl-1,3-dithian-7-yl)-1-heptynyl] trimethylsilane (1 equiv.) in 10% aqueous methanol (0.1 M) was cooled in an ice-bath and bis(trifluoroacetoxy)iodobenzene (1.5 equiv.) was added portionwise with stirring. The reaction mixture was stirred for an additional 10 min and poured into sodium bicarbonate solution. The mixture was extracted with diethyl ether, ether extracts were combined, dried and solvent removed to afford an oil which was chromatographed on silica gel to afford the title compound in 90% yield.

Anal. calcd. for $C_{18}H_{26}O_3Si$ C, 67.88; H, 8.23; found C, 67.56; H, 8.55

[7-(3,5-Dimethoxyphenyl)-7-methyl-1-octynyl]trimethylsilane.

[7-(3,5-Dimethoxyphenyl)-7-oxo-1-heptynyl]trimethylsilane (1 equiv.) was dissolved in anhydrous ether (0.5 M), the solution was cooled in an ice-bath under argon and methylmagnesium bromide (2 equiv., 3M solution in diethyl ether) was added dropwise. The light gray solution was allowed to warm to room temperature and stirred for an additional hour. The reaction mixture was poured into saturated ammonium chloride solution, the organic phase was separated and the aqueous phase was extracted with diethyl ether. The combined organic extracts were dried and ether removed to afford pure [7-(3,5-dimethoxyphenyl)-7-hydroxy-1-octynyl]trimethylsilane as a viscous oil after passing through a short silica gel column, in 95% yield.

The above carbinol (1 equiv.) was dissolved in anhydrous carbon tetrachloride (0.5 M) and dry hydrogen chloride gas was bubbled through for 1 hour. The solution was transferred to a separatory funnel with the aid of more carbon tetrachloride, washed with water and 10% sodium bicarbonate solution. The organic phase was dried and rotary evaporated to afford an oil which was passed through a short silica gel column to give pure [7-chloro-7-(3,5-dimethoxyphenyl)-1-octynyl]trimethylsilane.

A solution of the above chloride (1 equiv.) in dry toluene was cooled to –30° C. under argon and trimethylaluminum (2 equiv., 2M solution in toluene) was added in a slow dropwise manner. The resulting clear reaction mixture was stirred at room temperature for about 16 hours and then 5% aqueous hydrochloric acid was added in a very cautious manner. The organic layer was separated, washed with water, dried and toluene removed. The residual oil was chromatographed on silica gel to afford the title compound as colorless oil.

$^1$H NMR (CDCl$_3$) δ 6.47 (d, J=2.16 Hz, 2H), 6.28 (t, J=2.16 Hz, 1H), 3.78 (s, 6H), 2.14 (t, J=7.08 Hz, 2H), 1.63-1.06 [overlapping patterns i.e., 1.63-1.06 (m, 6H), 1.25 (s, 6H)], 0.10 (s, 9H).

Anal. calcd. for $C_{20}H_{32}O_2Si$ C, 72.23; H, 9.70; found C, 71.98; H, 9.87.

7-(3,5-Dimethoxyphenyl)-7-methyl-1-octyne.

[7-(3,5-Dimethoxyphenyl)-7-methyl-1-octynyl]trimethylsilane (1 equiv.) was dissolved in anhydrous methanol (0.8 M), anhydrous potassium carbonate (0.2 equiv.) was added and the heterogeneous mixture was stirred at room temperature, under argon, for 24 hours. The reaction mixture was diluted with water and extracted with diethyl ether. The ether extract was dried, concentrated by rotary evaporation and the residue was purified by chromatography on silica gel (5% diethyl ether-petroleum ether) to give the title compound in 76% yield.

3-(1,1-Dimethylhept-6-ynyl)resorcinol, (Compound 1.5)

A solution of 7-(3,5-dimethoxyphenyl)-7-methyl-1-octyne (1 equiv.) in anhydrous dichloromethane (0.1 M) was cooled to –40° C. under argon and boron tribromide (2.5 equiv., 1M solution in dichloromethane) was added via syringe. The reaction mixture was allowed to warm to 0° C. with stirring over a period of 1-1.5 hours and then quenched with saturated sodium bicarbonate. The organic layer was separated, dried and solvent removed. The residue was chromatographed on silica gel (30-40% diethyl ether-petroleum ether) to give the title resorcinol in 56% yield.

$^{13}$C NMR (CDCl$_3$) δ 156.37, 153.11, 105.92, 100.11, 84.76, 68.22, 55.30, 43.77, 37.70, 29.03, 28.79, 23.87, 18.24.

Procedure for the Synthesis of Resorcinol Compound 1.57:

N-(3,5-Dimethoxy-phenyl)-4-methyl-benzenesulfonamide.

A mixture of 3,5-dimethoxyaniline (24.0 g, 156.9 mmol) and p-toluenesulfonyl chloride (29.8 g, 156.9 mmol) in anhydrous pyridine (70 mL) was stirred and heated to reflux for 30 min under argon atmosphere. The reaction mixture was cooled to room temperature and poured into 400 mL of ice-cold water. Dichloromethane was added to extract the product. The organic layer was separated and washed with water, 5% HCl aqueous solution, water and brine and dried with anhydrous Na$_2$SO$_4$. Removal of solvent provided yellow solid crude, which was purified by re-crystallization in diethyl ether to afford 42.6 g (89.0%) of the title compound as light yellow crystalline solid. mp 103-104° C.

$^1$H NMR (CDCl$_3$) δ 7.74 (d, J=9.2 Hz, 2H), 7.26 (d, J=9.2 Hz, 2H), 6.94 (s, 1H), 6.26 (d, J=2.2 Hz, 2H), 6.17 (d, J=2.2 Hz, 1H), 3.70 (s, 6H), 2.38 (s, 3H); MS m/e 307 (M$^+$).

N-(3,5-Dimethoxy-phenyl)-N-heptyl-4-methyl-benzenesulfonamide.

A mixture of N-(3,5-Dimethoxy-phenyl)-4-methyl-benzenesulfonamide (15.0 g, 48.9 mmol), 1-bromoheptane (9.63 g, 53.8 mmol) and potassium carbonate (17.1 g, 124.2 mmol) in anhydrous DMF (100 mL) was stirred and heated at 120 °C. for 4 h, and then cooled to room temperature and poured into ice-cold water (400 mL). Diethyl ether (400 mL) was added to extract the product. The ethereal solution was separated and washed with water, brine and dried with Na$_2$SO$_4$. Removal of solvent and drying reagent provided 19.50 g of light yellow liquid, which was treated with small amount of diethyl ether to give 19.10 g (96.4%) of the title compound as a white solid upon cooling.

$^1$H NMR (CDCl$_3$) δ 7.53 (d, J=8.1 Hz, 2H), 7.25 (d, J=8.1 Hz, 2H), 6.39 (t, J=2.1 Hz 1H), 6.20 (d, J=2.1 Hz, 2H), 3.71 (s, 6H), 3.44 (t, J=7.0 Hz, 2H), 2.42 (s, 3H), 1.43-1.40 (m, 2H), 1.29-1.21 (m, 8H), 0.85 (t, J=7.1 Hz, 3H); MS m/e 405 (M$^{30}$).

N-(3,5-Dihydroxy-phenyl)-N-heptyl-4-methyl-benzenesulfonamide, (Compound 1.57).

Boron trichloride solution (145 mL, 1.0 M in CH$_2$Cl$_2$) was added dropwise to a solution of N-(3,5-Dimethoxy-phenyl)-N-heptyl-4-methyl-benzenesulfonamide (19.0 g, 47 mmol) and tetrabutylammonium iodide (53.5 g, 145 mmol) in 250 mL of anhydrous dichloromethane at –78° C. under argon atmosphere. The reaction mixture was stirred at –78° C. for 20 minutes, and then at 0° C. for 2 h. The reaction was quenched by addition of 100 mL of water slowly. The organic layer was separated and washed with water, 30% aqueous NaHSO$_3$ solution, water and brine, and dried over anhydrous sodium sulfate. Removal of solvent and drying reagent provided 50.83 g of a semi-solid crude product. This material was chromatographed on silica gel column eluted with a mixture of petroleum ether and acetone (2:1) to afford 16.83 g (94.6%) of the title compound as a light yellow solid.

$^1$H NMR (CDCl$_3$) δ 7.55 (d, J=8.1 Hz, 2H), 7.27 (d, J=8.1 Hz, 2H), 6.50 (bs, 2H), 6.35 (t, J=1.6 Hz 1 H), 6.24 (d, J=1.6 Hz, 2H), 3.41 (t, J=7.2 Hz, 2H), 2.40 (s, 3H), 1.43-1.38 (m, 2H), 1.27-1.19 (m, 8H), 0.84 (t, J=7.0 Hz, 3H), MS m/e 377 (M$^{30}$).

Resorcinol compound 1.55 (shown in Scheme 3) was synthesized by the method disclosed in Lu D. et al. *J. Med. Chem.*, 48: 4576 (2005) and in Dominianni S. J et al. *J. Org. Chem.*, 42: 344 (1977) the contents of each of which are hereby incorporated by reference.

2. Bicyclic Cannabinoid Synthesis

The bicyclic ketones (compound 2 with, for example, R groups 1, 2, 3, 4, 5, 9, 10, 11, 12, 13, 14, 15, 16, 17, 29, 30, 31, 34, 36, 38, 39, 40, 42, 43, 44, 45, 46, 55, 56 or 57 shown in Scheme 3) were synthesized by the method depicted in Scheme 3.

Scheme 3

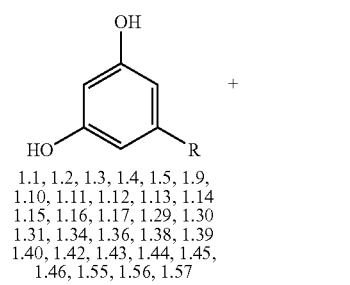

1.1, 1.2, 1.3, 1.4, 1.5, 1.9,
1.10, 1.11, 1.12, 1.13, 1.14
1.15, 1.16, 1.17, 1.29, 1.30
1.31, 1.34, 1.36, 1.38, 1.39
1.40, 1.42, 1.43, 1.44, 1.45,
1.46, 1.55, 1.56, 1.57

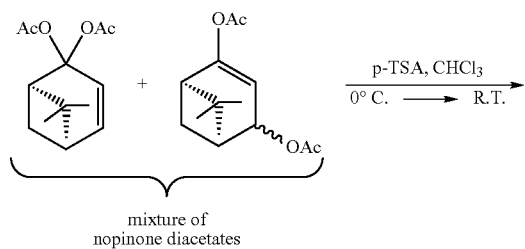

mixture of nopinone diacetates

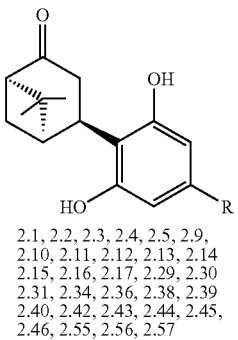

2.1, 2.2, 2.3, 2.4, 2.5, 2.9,
2.10, 2.11, 2.12, 2.13, 2.14
2.15, 2.16, 2.17, 2.29, 2.30
2.31, 2.34, 2.36, 2.38, 2.39
2.40, 2.42, 2.43, 2.44, 2.45,
2.46, 2.55, 2.56, 2.57

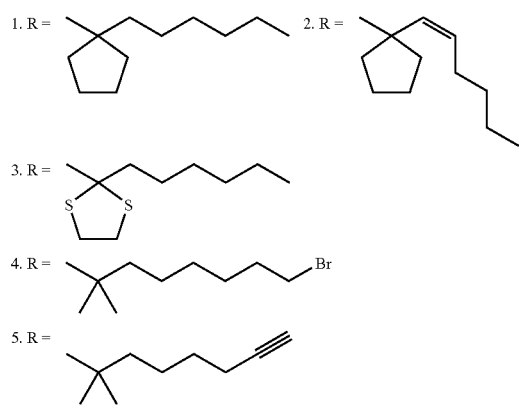

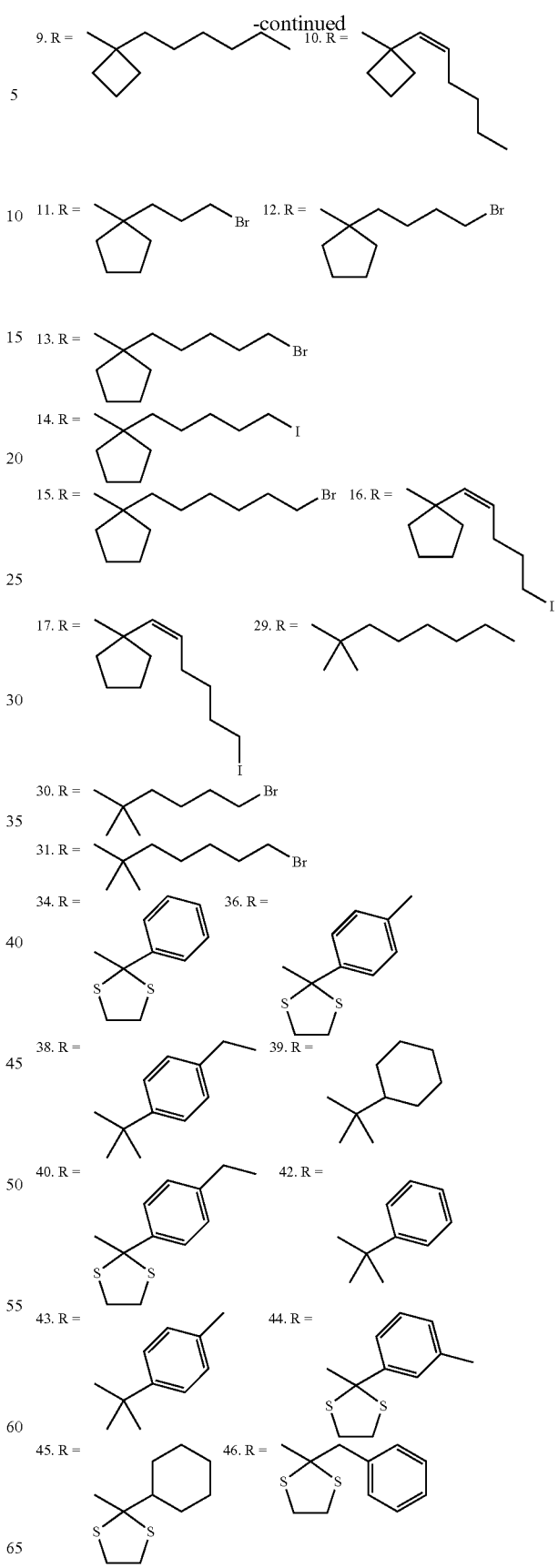

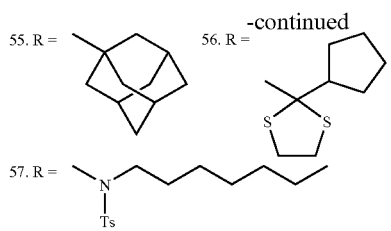

General Procedure:

To a solution of resorcinol (1 equiv.) and nopinone diacetates (approximately 1.3 equiv., ca. 87% pure by $^1$H NMR) in chloroform (approximately 0.1M) at 0° C. was added p-toluene sulfonic acid monohydrate (approximately 1.3 equiv.). Following the addition, the reaction temperature was raised to room temperature and stirring was continued for 4 hours to 3 days to ensure complete formation of the product. The reaction mixture was diluted with an organic solvent and washed sequentially with water, saturated aqueous sodium bicarbonate, and brine. The organic phase was dried over MgSO$_4$ and the solvent was removed under reduced pressure. The residue was chromatographed on silica gel to afford the bicyclic ketone.

Selected data of synthesized bicyclic ketones:

Compound 2.1

(4R)-4-[4-(1',1'-Cyclopentylheptyl)-2,6-dihydroxyphenyl]-6,6-dimethyl-2-norpinanone. Yield: 49%; white solid; mp=187-188° C.

Compound 2.2

(4R)-4-[4-(1',1'-Cyclopentylhept-2'-enyl)-2,6-dihydroxyphenyl]-6,6-dimethyl-2-norpinanone. Yield: 47%; white solid; mp=167-168° C.

Compound 2.3

(4R)-4-[4-(2-Hexyl-1,3-dithiolan-2-yl)-2,6-dihydroxyphenyl]-6-dimethyl-2-norpinanone. Yield: 13%; white solid; mp=160-161° C. dec.

$^1$H NMR (500 MHz, CDCl$_3$) δ: 6.68(s, 2H, ArH), 5.02(brs, 2H, OH), 3.95(t, J=8.2 Hz, 1H), 3.44 (dd, J=18.7 Hz, J=7.8 Hz, 1H), 3.37-3.30 (m, 2H), 3.25-3.18 (m, 2H), 2.60 (dd, J=19.5 Hz, J=8.5 Hz, 1H), 2.58 (t, J=4.7 Hz, 1H), 2.53-2.49 (m, 1H), 2.44 (d, J=10.8 Hz, 1H), 2.30 (m, 1H), 2.26-2.22 (m, 2H), 1.36 (s, 3H), 1.27-1.19 (m, 8H), 0.99 (s, 3H), 0.85 (t, J=6.5 Hz, 3H).

Compound 2.4

(4R)-4-[4-(7'-Bromo-1',1'-dimethylheptyl)-2,6-dihydroxyphenyl]-6,6-dimethyl-2-norpinanone. Yield: 41%; light yellow solid.

Anal. calcd. for $C_{24}H_{34}BrO_2$ C, 63.85; H, 7.81; found C, 63.99; H, 8.20.

Compound 2.15

(4R)-4-{4-[1-(6-Bromo-hexyl)-cyclopent-1-yl]-2,6-dihydroxyphenyl}-6,6-dimethyl-2-norpinanone. Yield: 52%; white solid; mp=156-158° C.

HRMS calcd for $C_{26}H_{37}BrO_3$ 476.1926; found 476.1931.

Compound 2.5

(4R)-4-[4-(1',1'-Dimethylhept-6'-ynyl)-2,6-dihydroxyphenyl]-6,6-dimethyl-2-norpinanone. Yield: 40%. The title compound (2.5) was used in the preparation of the derivative compound 4e.

FAB HRMS calcd for $C_{24}H_{32}O_3$ 369.2430 (M+H$^+$); found 369.2430.

Compound 2.34

(4R)-4-[4-(2-Phenyl-1,3-dithiolan-2-yl)-2,6-dihydroxyphenyl]-6,6-dimethyl-2-norpinanone. Yield: 16%; white foam.

$^1$H NMR (400 MHz, CDCl$_3$) δ: 7.60 (d, J=7.2 Hz, 2H), 7.30-7.21(m, 3H), 6.57 (s, 2H), 4.87 (brs, 2H, OH), 3.93(t, J=8.0 Hz, 1H), 3.45 (dd, J=18.7 Hz, J=7.8 Hz, 1H), 3.40 (bs, 4H), 2.58 (dd, J=8.8 Hz, 18.7 Hz, 1H), 2.57 (t, J=5.0 Hz, 1H), 2.50 (dt, J=5.5 Hz, J=10.5 Hz, 1 H), 2.46 (d, J=10.6 Hz, 1 H), 2.28 (t, J=2.5, 1H), 1.35 (s, 3H), 0.95 (s, 3H).

Compound 2.38

(4R)-4-[4-{1-(4-Ethyl-phenyl)-1,1-dimethyl}-2,6-dihydroxyphenyl]-6,6-dimethyl-2-norpinanone. Yield: 25%; mp=218-220° C.

$^1$H NMR (500 MHz, CDCl$_3$) δ: 7.14 (d, J=8.5 Hz, 2H), 7.11 (d, J=8.5 Hz, 2H), 6.17 (s, 2H), 4.80 (brs, 2H, OH), 3.93 (t, J=8.5 Hz, 1H), 3.47 (dd, J=19.0 Hz, J=8.0 Hz, 1H), 2.62 (q, J=7.5 Hz, 2H), 2.60-2.56 (m, 2H), 2.50 (dt, J=10.5 Hz, J=5.5 Hz, 1H), 2.44 (d, J=10.5 Hz, 1H), 2.28 (t, J=5.0 Hz, 1H), 1.59 (s, 6H), 1.35 (s, 3H), 1.23 (t, J=7.5 Hz, 3H), 0.98 (s, 3H).

Compound 2.55

(4R)-4-[4-(1-Adamantyl)-2,6-dihydroxyphenyl]-6,6-dimethyl-2-norpinanone. Yield: 67%; white solid; mp=284-286° C.

$^1$H NMR (400 MHz, CDCl$_3$) δ: 6.31 (s, 2H), 4.73 (s, 2H, OH), 3.95 (t, J=8.0 Hz, 1H), 3.48 (dd, J=18.5 Hz, J=7.8 Hz, 1H), 2.63 (dd, J=8.0 Hz, J=18.5 Hz, 1H), 2.59 (t, J=5.0 Hz, 1H), 2.52 (dt, J=11.0 Hz, J=5.5 Hz, 1H), 2.46 (d, J=11.0 Hz, 1H), 2.28 (t, J=5.0 Hz, 1H), 2.07 (bs, 3H), 1.83 (d, J=2.1 Hz, 6H), 1.78 (d, J=12.5 Hz, 3H), 1.71(d, J=12.5 Hz, 3H), 1.34 (s, 3H), 0.99 (s, 3H).

Compound 2.57

N-[4-(6,6-Dimethyl-4-oxo-bicyclo[3.1.1]hept-2-yl)-3,5-dihydroxy-phenyl]-N-heptyl-4-methyl-benzenesulfonamide. Yield: 33.5%; white solid; mp=192-193° C.

$^1$H NMR (CDCl$_3$) δ 7.55 (d, J=8.2 Hz, 2H), 7.26 (d, J=8.2 Hz, 2H), 6.12 (s, 2H), 5.79 (s, 2H), 3.95 (t, J=7.0 Hz, 1H), 3.44-3.32 (m, 3H), 2.60-2.50 (m, 3H), 2.44-2.41 (m, 1H), 2.40 (s, 3H), 2.29 (t, J=5.3 Hz, 1H), 1.42-1.38 (m, 2H), 1.37 (s, 3H), 1.26-1.18 (m, 8H), 1.0 (s, 3H), 0.84 (t, J=7.2 Hz, 3H), MS m/e 513 (M$^{30}$).

The cyano-substituted bicyclic ketones, (compounds 2 with, for example, R groups 18, 19, 22, 26, 23, 27, 32 or 33 shown in Scheme 4) were synthesized by the method depicted in Scheme 4.

Scheme 4

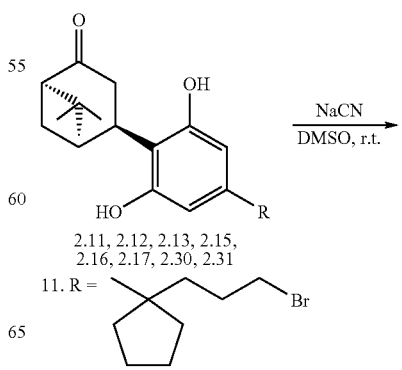

-continued

12. R = 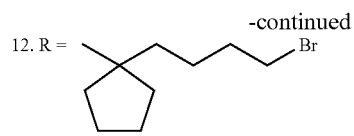

13. R = 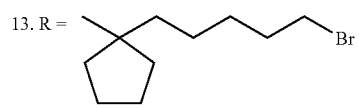

15. R = 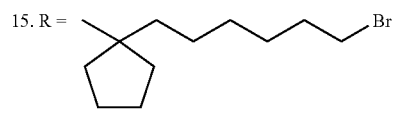

16. R = 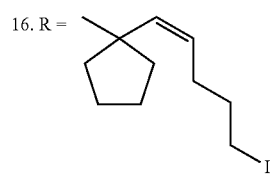

17. R = 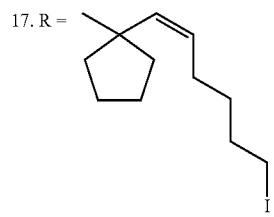

30. R = 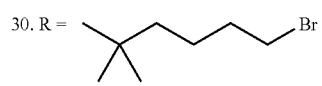

31. R = 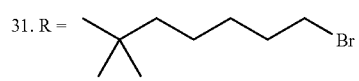

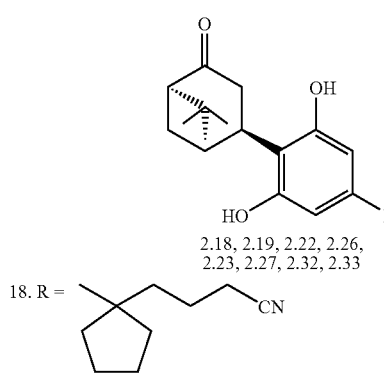
2.18, 2.19, 2.22, 2.26, 2.23, 2.27, 2.32, 2.33

18. R = 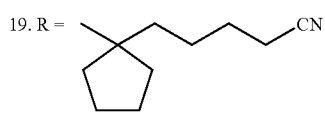

19. R =

22. R = 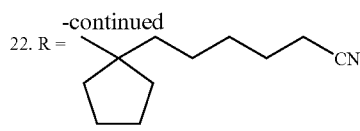

26. R = 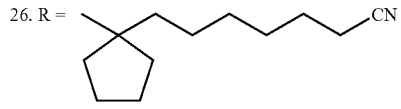

23. R = 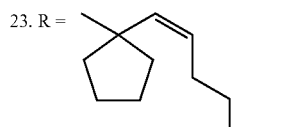

27. R = 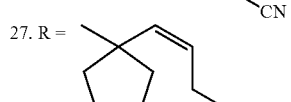

32. R = 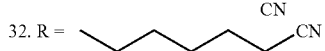

33. R = 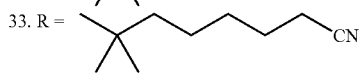

General Procedure:

To a stirred suspension of sodium cyanide (1.2 equiv.) in DMSO at room temperature was added a solution of starting bromo- or iodo-substituted bicyclic ketone (1.0 equiv.) in DMSO over a period of 10 min. The reaction mixture was stirred vigorously overnight and then quenched by adding ice, saturated aqueous NaCl and diethyl ether. The organic layer was separated and the aqueous phase was extracted with diethyl ether. The combined organic layer was washed with brine, dried over MgSO$_4$ and the solvent was evaporated under reduced pressure. The residue purified by flash column chromatography (diethyl ether-petroleum ether) on silica gel to give the cyano substituted bicyclic ketones.

Selected data of synthesized cyano-substituted bicyclic ketones:

Compound 2.19
(4R)-4-{4-[1-(4-Cyano-butyl)-cyclopent-1-yl]-2,6-dihydroxyphenyl}-6,6-dimethyl-2-norpinanone. Yield: 51%; white solid; mp=179-181° C.; IR: v=2251 cm$^{-1}$ (CN), 1683 cm$^{-1}$ (C=O).
HRMS calcd for C$_{25}$H$_{33}$NO$_3$ 395.2460; found 395.2464.

Compound 2.22
(4R)-4-{4-[1-(5-Cyano-pentyl)-cyclopent-1-yl]-2,6-dihydroxyphenyl}-6,6-dimethyl-2-norpinanone. Yield: 53%; white solid; mp=165-168° C.; IR: v=2248 cm$^{-1}$ (CN), 1683 cm$^{-1}$ (C=O).
HRMS calcd for C$_{26}$H$_{35}$NO$_3$ 409.2617; found 409.2611.

Compound 2.23
(4R)-4-{4-[1-(1,2-cis-5-Cyano-penten-1-yl)-cyclopent-1-yl]-2,6-dihydroxyphenyl}-6,6-dimethyl-2-norpinanone. Yield: 50%; white solid; mp=112-114° C.; IR: v=2251 cm$^{-1}$ (CN), 1683 cm$^{-1}$ (C=O).
HRMS calcd for C$_{26}$H$_{33}$NO$_3$ 407.2460; found 407.2464.

The azido and isothiocyanato substituted bicyclic ketones (compound 2 with for example, R groups 54, 20, 25, 28, 24, 52, 53 or 21 shown in Scheme 5) were synthesized by the method depicted in Scheme 5.
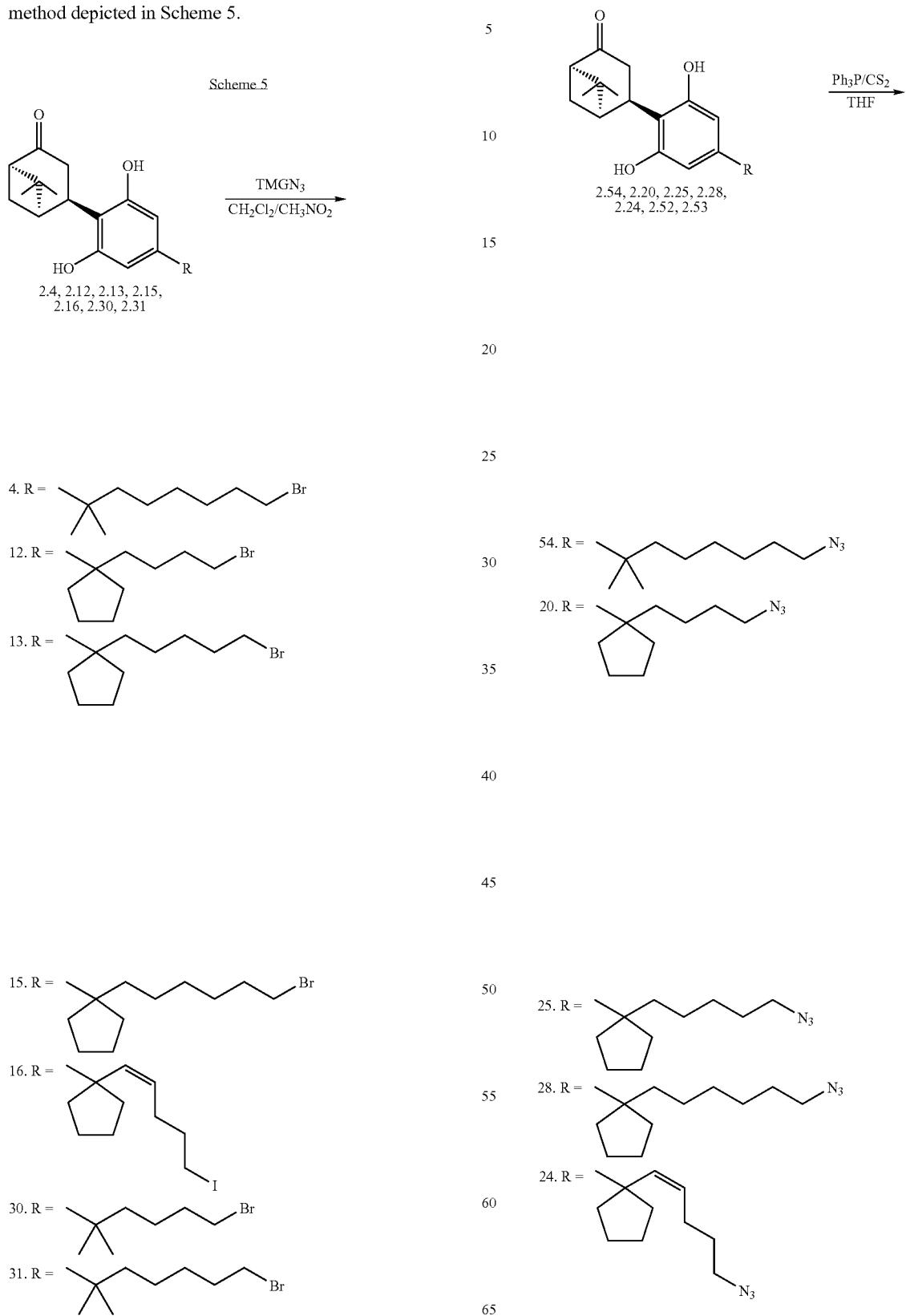

-continued

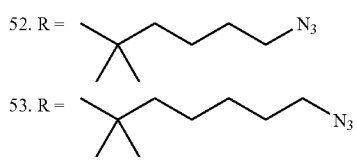

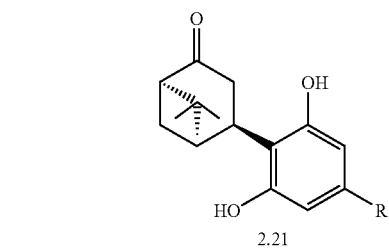

2.21

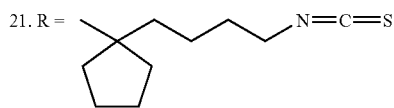

General Procedure:

A solution of starting bromo or iodo substituted bicyclic ketone (1 equiv.) in dry $CH_2Cl_2/CH_3NO_2$ was added dropwise to a solution of tetramethylguanidinium azide (2 equiv.) in dry $CH_2Cl_2$ at 0° C. under nitrogen. The resulting mixture was allowed to reach room temperature and refluxed overnight. Subsequently, the solvent was removed under reduced pressure and diethyl ether was added until no more 10 precipitate was formed. The precipitate was filtered out, and the filtrate was dried over sodium sulfate. Removal of the solvent yielded the crude azido substituted bicyclic ketone which was purified by column chromatography (diethyl ether in hexane as eluent).

Selected data of synthesized azido-substituted bicyclic ketones:

Compound 2.54

(4R)-4-[4-(7'-Azido-1',1'-dimethylheptyl)-2,6-dihydroxyphenyl]-6,6-dimethyl-2-norpinanone.

$^1$H NMR (500 MHz, $CDCl_3$) δ: 6.27 (s, 2H), 5.20 (brs, 2H, OH), 3.95 (t, J=8.0 Hz, 1H), 3.51 (dd, J=19.0 Hz, J=8.0 Hz, 1H), 3.23 (t, J=7.0 Hz, 2H), 2.63 (dd, J=8.5 Hz, J=18.5 Hz, 1H), 2.59 (t, J=5.0 Hz, 1H), 2.52 (dt, J=11.0 Hz, J=5.5 Hz, 1H), 2.47 (d, J=11 Hz, 1H), 2.31 (t, J=5.5 Hz, 1H), 1.56-1.48 (m, 4H), 1.36 (s, 3H), 1.35-1.29 (m, 2H), 1.26-1.20 (m, 2H), 1.20 (s, 6H), 1.06-1.10 (m, 2H), 0.99 (s, 3H).

Compound 2.20

(4R)-4-{4-[1-(4-Azido-butyl)-cyclopent-1-yl]-2,6-dihydroxyphenyl}-6,6-dimethyl-2-norpinanone. Yield: 78%; white solid; mp=151-153° C. The title compound (2.20) was used in the preparation of compound 2.21.

HRMS calcd for $C_{24}H_{33}N_3O_3$ 411.2522; found 411.2529.

Compound 2.28

(4R)-4-{4-[1-(6-Azido-hexyl)-cyclopent-1-yl]-2,6-dihydroxyphenyl}-6,6-dimethyl-2-norpinanone. Yield: 75%; white solid; mp=123-125° C.; IR: v=2090 cm$^{-1}$ ($N_3$).

HRMS calcd for $C_{26}H_{37}N_3O_3$ 439.2835; found 439.2840.

Compound 2.24

(4R)-4-{4-[1-(1,2-cis-5-Azido-penten-1-yl)-cyclopent-1-yl]-2,6-dihydroxyphenyl}-6,6-dimethyl-2-norpinanone. Yield: 77%; white solid; mp=114-115° C.

HRMS calcd for $C_{25}H_{33}N_3O_3$ 423.2522; found 423.2515.

Compound 2.52

(4R)-4-[4-(5'-Azido-1',1'-dimethylpentyl}-2,6-dihydroxyphenyl]-6,6-dimethyl-2-norpinanone.

$^1$H NMR (500 MHz, $CDCl_3$) δ: 6.28 (s, 2H), 5.52 (brs, 2H, OH), 3.95 (t, J=8.5 Hz, 1H), 3.53 (dd, J=18.0 Hz, J=8.0 Hz, 1H), 3.20 (t, J=7 Hz, 2H), 2.66-2.49 (m, 4H), 2.31 (t, J=5.0 Hz, 1H), 1.54-1.51 (m, 4H), 1.36 (s, 3H), 1.20 (s, 6H), 1.1 (m, 2H), 0.99 (s, 3H).

Compound 2.53

(4R)-4-[4-(6'-Azido-1',1'-dimethylhexyl)-2,6-dihydroxyphenyl]-6,6-dimethyl-2-norpinanone.

$^1$H NMR (500 MHz, $CDCl_3$) δ: 6.28 (s, 2H), 5.43 (brs, 2H, OH), 3.95 (t, J=8.5 Hz, 1H), 3.53 (dd, J=18.0 Hz, J=8.0 Hz, 1H), 3.20 (t, J=7 Hz, 2H), 2.66-2.46 (m, 4H), 2.31 (t, J=5.0 Hz, 1H), 1.56-1.48 (m, 4H), 1.35 (s, 3H), 1.27 (m, 2H), 1.19 (s, 6H), 1.09 (m, 2H), 0.99 (s, 3H).

Compound 2.21

(4R)-4-{4-[1-(4-Isothiocyanato-butyl)-cyclopent-1-yl]-2,6-dihydroxyphenyl}-6,6-dimethyl-2-norpinanone.

Procedure:

Starting material (compound 2.20, 1 equiv.) and carbon disulfide (30 equiv.) were dissolved in anhydrous THF. The mixture was stirred at room temperature, and triphenylphosphine (1.7 equiv.) was added. After 3 days, the solvent was evaporated under vacuum, and the residue was purified by column chromatography (70% diethyl ether-hexane) to give the product 2.21. Yield: 71%; white foam; IR: v=2091 cm$^{-1}$ (NCS), 1681 cm$^{-1}$ (C=O).

The bicyclic cannabinoids 2.6, 2.7 and 2.8 (shown in Scheme 6) were synthesized from the bicyclic ketone 2.2 following the method depicted in Scheme 6.

Scheme 6

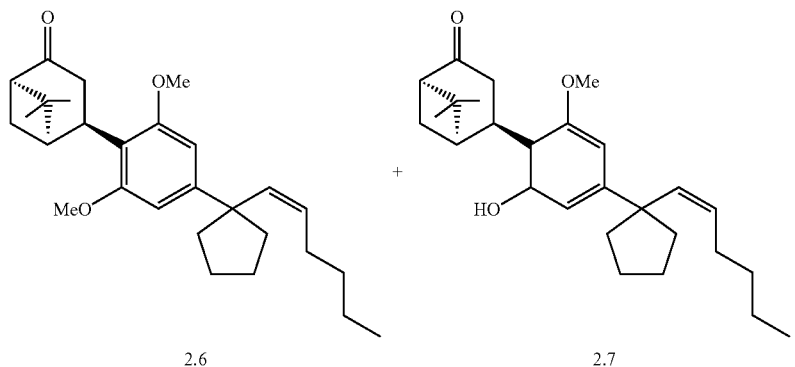

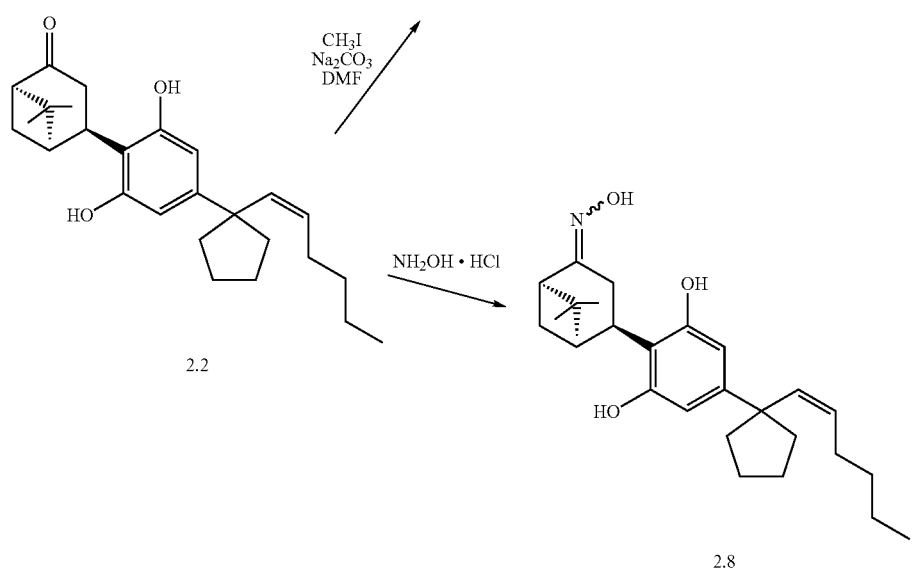

Procedure:

To a mixture of 2.2 (1 equiv.) and Na₂CO₃ (10 equiv.) in anhydrous DMF at room temperature under an argon atmosphere was added methyl iodide (3 equiv.). The resulting mixture was stirred at room temperature and then diluted with diethyl ether and water. The organic phase was separated, the aqueous phase extracted with diethyl ether and the combined organic layer washed with brine, dried (MgSO₄) and evaporated. Purification by flash column chromatography (diethyl ether-hexane) afforded compounds 2.6 and 2.7.

To a stirred aqueous solution of hydroxylamine hydrochloride and potassium hydroxide at 0° C. was added (4R)-4-[4-(1',1'-cyclopentylhept-2'-enyl)-2,6-dihydroxyphenyl]-6,6-dimethyl-2-norpinanone (2.2). Stirring was continued for 4 hours and then the reaction mixture was diluted with water and ethyl acetate. The organic layer was separated the aqueous phase extracted with ethyl acetate and the combined organic layer dried (MgSO₄) and evaporated to leave compound 2.8 in 75% yield.

The bicyclic diketones (compound 2 with for example, R groups 35, 37, 41, 47 or 48 shown in Scheme 7) were synthesized by the method depicted in Scheme 7.

Scheme 7

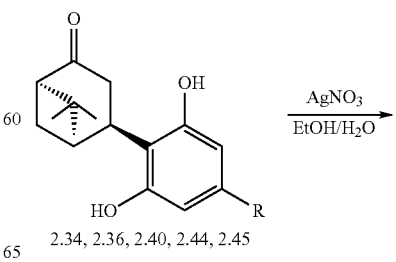

-continued

34. R = 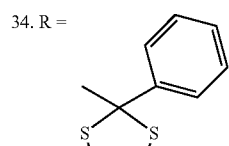

36. R = 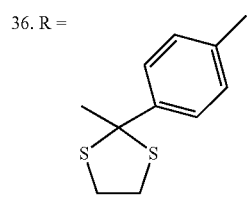

40. R = 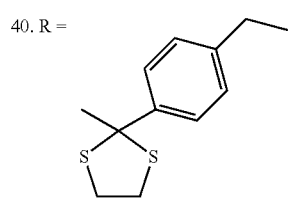

44. R = 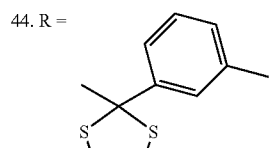

45. R = 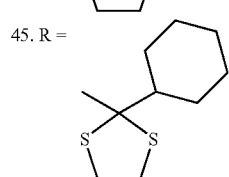

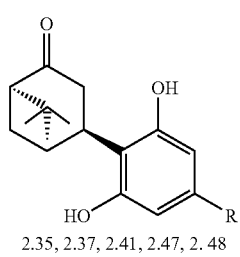
2.35, 2.37, 2.41, 2.47, 2.48

35. R = 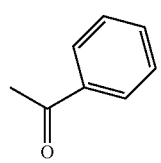

37. R = 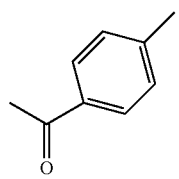

-continued

41. R = 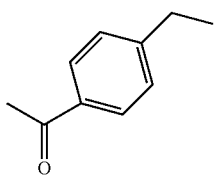

47. R = 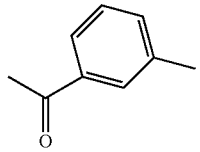

48. R = 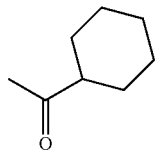

General Procedure:

To a stirred solution of 1,3 dithiolane cannabinoid (1 equiv.) in 90% ethanol at room temperature was added a solution of $AgNO_3$ (3 equiv) in water and the reaction mixture was stirred at room temperature for 3-4 h. At completion the precipitate was removed and washed with ethyl acetate, and the filtrate further diluted with ethyl acetate and washed with brine and then dried ($MgSO_4$). Evaporation of volatiles under reduced pressure followed by flash column chromatography gave desired bicyclic diketones in 90-95% yield.

Selected data of synthesized bicyclic diketones:

Compound 2.35

(4R)-4-[4-(Benzoyl)-2,6-dihydroxyphenyl]-6,6-dimethyl-2-norpinanone. Yield: 90%; white solid; mp=258-259° C. dec.

$^1$H NMR (400 MHz, $CDCl_3$) δ: 7.77 (dd, J=1.3 Hz, 8.4 Hz, 2H), 7.67 (bs, 2H, OH), 7.55 (t, J=1.3 Hz, 7.4 Hz, 1H), 7.44 (t, J=7.4 Hz, 2H), 6.84 (s, 2H), 4.13 (t, J=8.2 Hz, 1H), 3.64 (dd, J=18.7, J=7.8 Hz, 1H), 2.63-2.49 (m, 4H), 2.33 (t, J=5.5, 1H), 1.37 (s, 3H), 1.02 (s, 3H).

Compound 2.48

(4R)-4-[4-(Cyclohexanecarbonyl)-2,6-dihydroxyphenyl]-6,6-dimethyl-2-norpinanone. Yield: 92%; white solid; mp=249-251° C.

The bicyclic ketones 2.49, 2.50 and 2.51 (shown in Scheme 8) were synthesized by the method depicted in Scheme 8.

Scheme 8

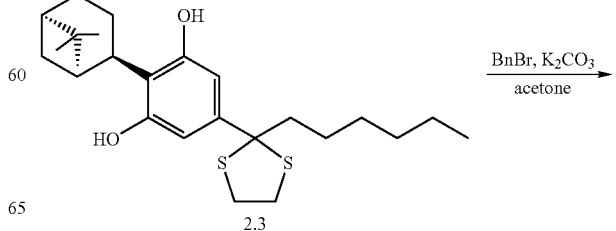
2.3

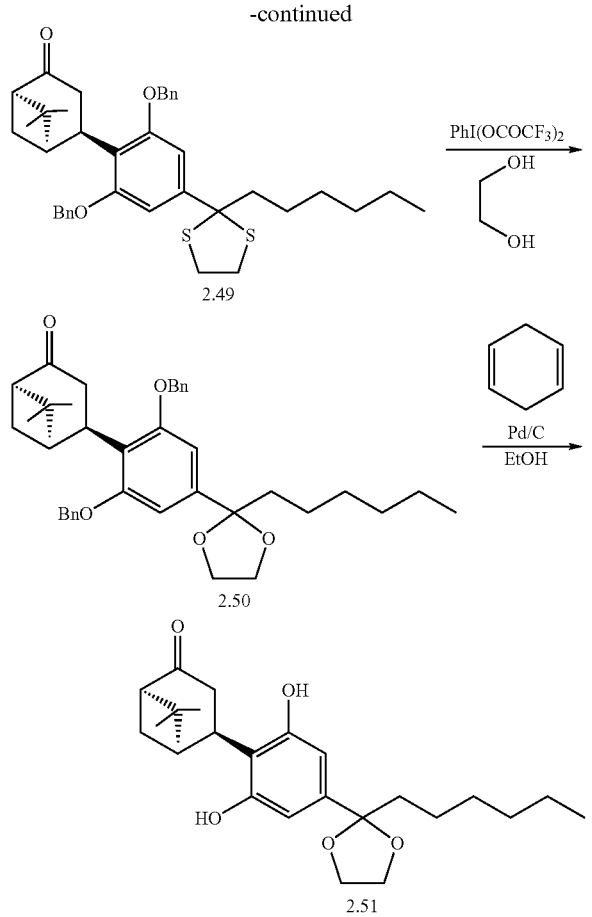

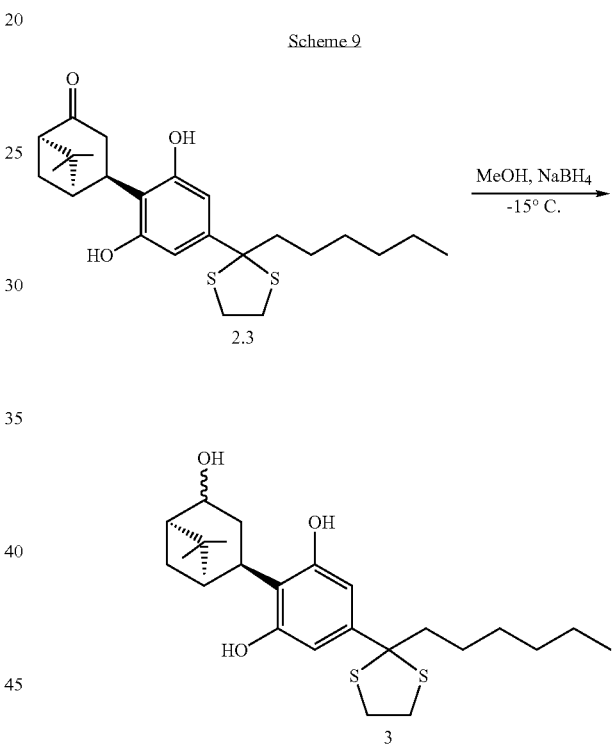

hexane) to give 62 mg (81% yield) of (4R)-4-[4-(2-hexyl-1,3-dioxolane-2-yl)-2,6-dihydroxyphenyl]-6,6-dimethyl-2-norpinanone (compound 2.51). White solid; mp=185-186° C.
$^1$H NMR (500 MHz, CDCl$_3$) δ 6.44 (s, 2H, ArH), 5.40 (br s, 2H, OH), 4.02-3.97 (m, 3H), 3.81-3.78 (m, 2H), 3.52 (dd, J=18.7 Hz, J=7.8 Hz, 1H), 2.62 (dd, J=19.5 Hz, J=8.5 Hz, 1H), 2.60 (t, J=4.7 Hz, 1 H), 2.54-2.49 (m, 1H), 2.47 (d, J=10.8 Hz, 1H), 2.30 (m as t, J=5.2 Hz, 1H), 1.85-1.80 (m, 2H), 1.37 (s, 3H, 6-Me), 1.34-1.18 (m, 8H), 1.01 (s, 3H, 6-Me), 0.84 (t, J=6.5 Hz, 3H).

Compound 3

Synthesis of a diastereomeric mixture of (4R)-4-[4-(2-hexyl-1,3-dithiolan-2-yl)-2,6-dihydroxyphenyl]-6,6-dimethyl-2β-norpinanol and (4R)4-[4-(2-hexyl-1,3-dithiolan-2-yl)-2,6-dihydroxyphenyl]-6,6-dimethyl-2α-norpinanol.

The title mixture (compound 3) was synthesized by the method depicted in Scheme 9 below.

Procedure:

To a solution of 2.3 (350 mg, 0.806 mmol) and benzyl bromide (411 mg, 2.418 mmol) in anhydrous acetone (27 ml) at room temperature under an argon atmosphere was added K$_2$CO$_3$. The reaction mixture was stirred at 40°-50° C. overnight and then diluted with acetone. The insoluble materials were filtered out, the filtrate was evaporated and the residue obtained purified by flash column chromatography (27% diethyl ether-hexane) to give 474 mg (96% yield) of compound 2.49 which was used in the preparation of compound 2.50.

To a mixture of 2.49 (219 mg, 0.356 mmol), anhydrous ethylene glycol (3 ml) and anhydrous CH$_3$CN (5 ml) at 0° C. under an argon atmosphere was added bis(trifluoroacetoxy)iodobenzene (260 mg, 0.605 mmol). The resulting mixture was stirred for 5 minutes and then diluted with saturated aqueous NaHCO$_3$ solution and diethyl ether. The organic phase was separated, dried over MgSO$_4$ and the solvent was evaporated under reduced pressure. Purification by flash column chromatography (40% diethyl ether-hexane) gave compound 2.50 (61% yield) which was used in the preparation of compound 2.51.

To a suspension of 2.50 (110 mg, 0.189 mmol) and Pd/C (330 mg) in ethyl alcohol (10 ml) under an argon atmosphere was added 1,4-cyclohexadiene (1.4 ml). The resulting mixture was stirred at room temperature for 5 hours then diluted with ethyl acetate and the catalyst was removed by filtration. The filtrate was evaporated and the residue obtained was purified by flash column chromatography (40% ethyl acetate- Procedure:

To a stirred solution of (4R)-4-[4-(2-hexyl-1,3-dithiolan-2-yl)-2,6-dihydroxyphenyl]-6,6-dimethyl-2-norpinanone (compound 2.3) (11 mg, 0.025 mmol) in methanol (0.5ml) at −15° C. under an argon atmosphere was added sodium borohydride (3 mg 0.079 mmol). The reaction was stirred at the same temperature for 2.5 hours and upon completion was quenched by the addition of saturated aqueous ammonium chloride. The volatiles were removed in vacuum and the residue was extracted with ethyl acetate. The organic layer was washed with water and brine, dried over MgSO$_4$ and the solvent evaporated. The residue was chromatographed on silica gel to afford 6 mg (54%) of the title mixture as a white glassy.

Preparation of (1S,5R)-(−)-nopinone derived mixture of diacetates. Synthesis of bicyclic ketones of compound formula Ib.

The synthesis of compounds 2 shown in Scheme 3 was accomplished by the stereospecific condensation of a mixture of nopinone diacetates shown in Scheme 3 with an appropriately substituted resorcinol. On the other hand the requisite mixture of nopinone diacetates shown in Scheme 3 was prepared by the method disclosed in Drake et al. *J.Med. Chem.*, 3596 (1998). This method involves isopropenyl acetate based transesterification followed by lead tetraacetate oxidation with no loss of optical purity starting from commercially available (1R, 5S)-(+)-nopinone. Similarly the mixture of nopinone diacetates shown in Scheme 10 was synthesized from (1S, 5R)-(−)-nopinone. In turn (1S, 5R)-(−)-nopinone of high optical purity was synthesized by the method disclosed in Brown et al. *J. Org. Chem.* 1764 (1989) and in Brown et al. *J. Org. Chem.*, 1217 (1990) starting from commercially available (+)-α-pinene (Scheme 10). Each of the above references is incorporated by reference herein.

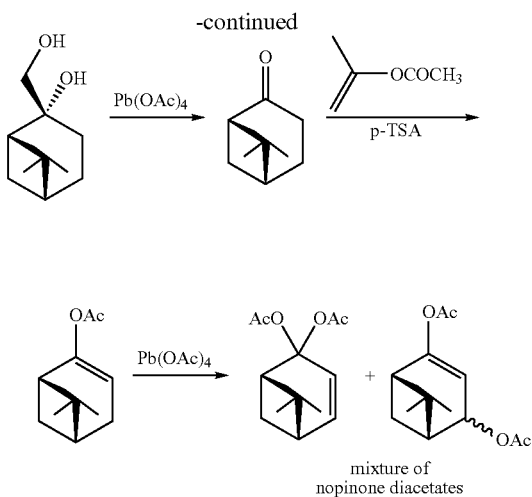

mixture of nopinone diacetates

Scheme 10

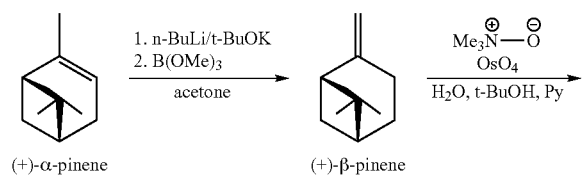

The enantiomer bicyclic ketones (compound formula Ib for example, compounds 2.2e, 2.14e, 2.29e or 2.22e) were synthesized using the mixture of nopinone diacetates of Scheme 10 and the method depicted in Scheme 11. The procedures in Scheme 11 are the same as the procedures in Schemes 3 and 4 used to prepare the counterpart bicyclic ketones of compound formula Ia, e.g. compounds 2.2, 2.14, 2.29 and 2.22.

Scheme 11

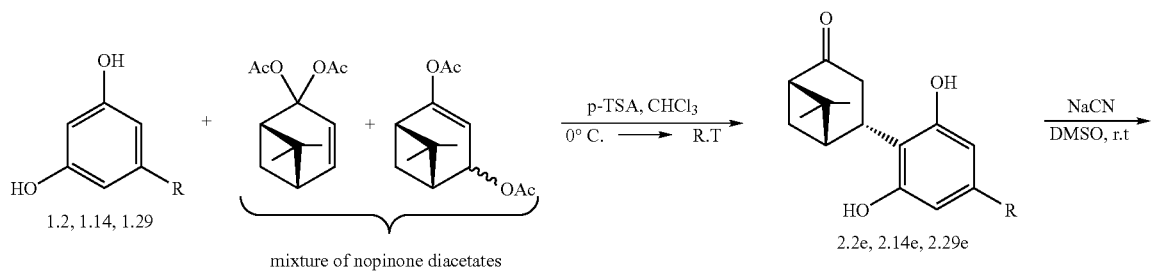

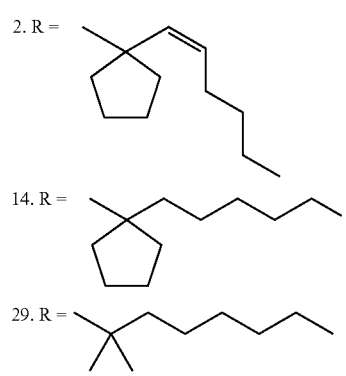

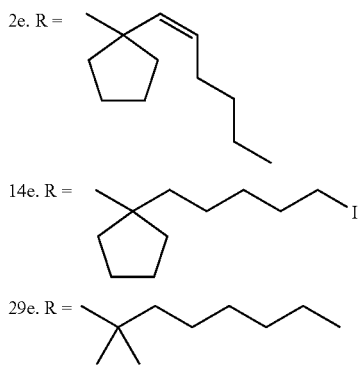

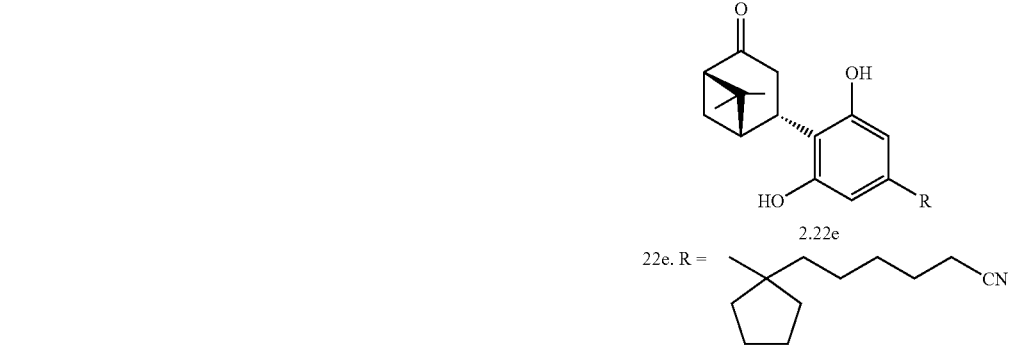

Those skilled in the art will recognize, or be able to ascertain with no more than routine experimentation, many equivalents to the specific embodiments disclosed herein. Such equivalents are intended to be encompassed by the claims.

What is claimed is:

1. A compound of formula Ia below, including physiologically acceptable salts, diastereomers, enantiomers, double bond isomers, or mixtures thereof;

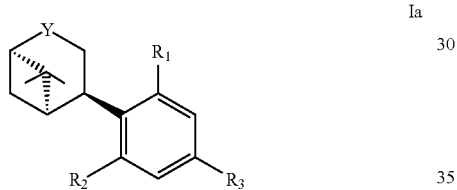

wherein:
Y is selected from >C=O, >CH—(CH$_2$)$_f$—Y$_1$—(CH$_2$)$_g$—Y$_2$, >C=N—Y$_3$, >CH—NY$_4$Y$_5$, >CH—(CH$_2$)$_h$—Y$_6$ or >C=CY$_7$Y$_8$, including all isomers, Y$_1$ is independently selected from O, CO, C(O)O, OC(O) or CH$_2$, Y$_2$ is independently selected from H, halogen, CN, CF$_3$, N$_3$, OH, NH$_2$, COOH, alkoxy, acyloxy, NCS or NCO, Y$_3$ is independently selected from —OH, —NH$_2$, alkoxy, alkyl, —(CH$_2$)$_n$—NR$_{10}$R$_{11}$, —(CH$_2$)$_n$—CO$_2$R (where R comprises H or alkyl), —O—(CH$_2$)$_n$—NR$_{10}$R$_{11}$, —O—(CH$_2$)$_n$—CO$_2$R (where R comprises H or alkyl) or —O—(CH$_2$)$_n$—CONR$_{10}$R$_{11}$, Y$_4$ is independently selected from H, OH, alkoxy or alkyl, Y$_5$ is independently selected from H, OH, alkoxy or alkyl, wherein Y$_4$ and Y$_5$ cannot both be OH and wherein Y$_4$ and Y$_5$ cannot both be alkoxy, Y$_6$ is independently selected from H, halogen, CN, COOH, NH$_2$, SO$_2$Cl, SO$_2$F, SO$_3$H, COalkyl, CF$_3$, SO$_2$alkyl, COfluoroalkyl, N$_3$, OH, alkoxy, acyloxy, NCS or NCO, Y$_7$ and Y$_8$ are each independently selected from H, alkyl, alkenyl, CN, OH, alkoxy or —(CH$_2$)$_n$—NR$_{10}$R$_{11}$, R$_{10}$ and R$_{11}$ are each independently selected from H, alkyl, hydroxyalkyl, or R$_{10}$ and R$_{11}$ together comprise part of a 3 to 7 membered saturated heterocyclic ring containing up to one additional heteroatom selected from N, O and S, f is an integer from 0 to about 5, g is an integer from 0 to about 5, h is an integer from 0 to about 5, n is an integer from 0 to about 4, wherein when an integer is 0 the structural portion modified by that integer is absent and the adjacent subunits are directly connected;

R$_1$ and R$_2$ are each independently selected from H, OH, NH$_2$, NO$_2$, CN, OCOCH$_3$, OC(O)CH=CHCOOH, halogen, alkyl, —O-alkyl, acyl, aroyl, benzoyl, substituted benzoyl, phenacyl, substituted phenacyl, —O-alkyl-aryl, —O-alkyl-NR$_{10}$R$_{11}$, —O-alkyl-COOR (where R is selected from H or alkyl), —O-alkyl-CONR$_{10}$R$_{11}$, —N(alkyl)$_2$, —CO(alkyl)X or —OCO(alkyl)X or OCO(alkenyl)X (where X is selected from H, COOH, dialkylamino, a cyclic amine, a carbocyclic ring, a heterocyclic ring, an aromatic ring or a heteroaromatic ring), —O—P(O)(OR)$_2$ or —O—P(O)(OH)(OR) (where R is selected from H or alkyl), —P(O)(OR)$_2$ (where R is selected from H or alkyl), —P(O)(OH)(OR) (where R is selected from H or alkyl) or —OC(O)—CH(NH$_2$)—R$_{16}$ (where R$_{16}$ is selected from H, CH(OH)CH$_3$ or alkyl-X$_3$ and X$_3$ is selected from: H, —NH—C(=NH)NH$_2$, C(O)NH$_2$, COOH, SH, SCH$_3$, OH, NH$_2$, a substituted or unsubstituted aromatic ring, a substituted or unsubstituted heteroaromatic ring, a substituted or unsubstituted heterocyclic ring, R$_{10}$ and R$_{11}$ are each independently selected from H, alkyl, hydroxyalkyl or R$_{10}$ and R$_{11}$ together comprise part of a 3 to 7 membered saturated heterocyclic ring containing up to one additional heteroatom selected from N, O and S; and R$_3$ is selected from the following structures:

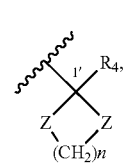

Ia 1

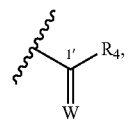

Ia 2

-continued

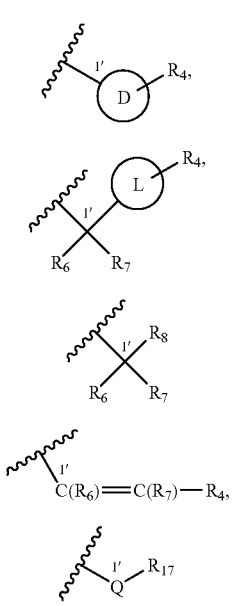

wherein each Z is independently selected from S, O, NH, N(CH$_3$), SO, SO$_2$, or CR$_{12}$R$_{13}$ where R$_{12}$ and R$_{13}$ are each independently selected from H or alkyl, W is selected from O, S or CR$_{12}$R$_{13}$ where R$_{12}$ and R$_{13}$ are each independently selected from H or alkyl, D is selected from a cycloalkyl ring, a heterocyclic ring, an adamantyl ring, an heteroadamantyl ring or any above ring optionally substituted by R$_4$ in any possible position with the proviso that ring D can not be bonded to R$_4$ from the 1' position, L is selected from a cycloalkyl ring, a heterocyclic ring, an aromatic ring, a heteroaromatic ring, an adamantyl ring, an heteroadamantyl ring or any above ring optionally substituted by R$_4$ in any possible position, R$_4$ is selected from —(CH$_2$)$_j$—R$_5$, —(CH$_2$)$_j$-A-(CH$_2$)$_k$—R$_5$ or —(CH$_2$)$_j$-A-(CH$_2$)$_k$—B—-R$_5$, A and B are each independently selected from —CH$_2$—CH$_2$—, —CH=CH—, —C≡C—, O, S, SO, SO$_2$ or NH, R$_5$ is selected from H, halogen, CN, CF$_3$, N$_3$, COOH, NH$_2$, N(CH$_3$)$_2$, ⊕N(CH$_3$)$_3$, Sn(alkyl)$_3$, phenyl, OH, NCS, NCO, NO$_2$, CHO, SO$_3$H, SO$_2$Cl, SO$_2$F, PO$_3$H$_2$, C(O)CF$_3$, SH, —CH=CH$_2$, —C≡CH, NH(alkyl), N(alkyl)$_2$, O-aryl, alkoxy, thioalkoxy, sulfonamide, COOR (where R is selected from H or alkyl), a substituted or unsubstituted carbocylic ring, a substituted or unsubstituted heterocyclic ring, a substituted or unsubstituted aromatic ring, a substituted or unsubstituted heteroaromatic ring, a polycarbocyclic ring structure having 2 to about 5 rings, a polyheterocyclic ring structure having 2 to about 5 rings or CONR$_{10}$R$_{11}$ (where R$_{10}$ and R$_{11}$ are each independently selected from H, alkyl, hydroxyalkyl, or R$_{10}$ and R$_{11}$ together comprise part of a 5 or 6 membered saturated heterocyclic ring containing up to one additional heteroatom selected from N, O and S), n is an integer from 0 to about 4,
j is an integer from 0 to about 7,
k is an integer from 0 to about 7, wherein when an integer is 0 the structural portion modified by that integer is absent and the adjacent subunits are directly connected, R$_6$ and R$_7$ are each independently selected from H or alkyl, R$_8$ is selected from —(CH$_2$)$_j$—C≡C—(CH$_2$)$_k$—R$_5$ or —(CH$_2$)$_j$—C(R$_6$)=C(R$_7$)—(CH$_2$)$_k$—R$_5$ where R$_5$, R$_6$ and R$_7$ are as previously defined, j is an integer from 0 to about 7, k is an integer from 0 to about , wherein when an integer is 0 the structural portion modified by that integer is absent and the adjacent subunits are directly connected, Q is selected from O, S, NH or N(R$_{18}$) (where R$_{18}$ is selected from SO$_2$-aryl, alkyl-R$_5$, aryl-R$_5$ or heteroaryl-R$_5$), R$_{17}$ is selected from alkyl-R$_5$, aryl-R$_5$ or heteroaryl-R$_5$;

with the following provisos:
if Y is C=O, and R$_1$ is selected from H, OH, OCH$_3$, NH$_2$, O(CH$_2$)$_n$N(CH$_3$)$_2$ (where n is an integer from 1-3) or

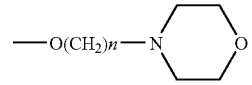

(where n is an integer between 1-3), and R$_2$ is selected from H, OH or OCH$_3$, then R$_3$ cannot be selected from (CH$_2$)$_n$C≡CH where n is an integer from 3-5 or

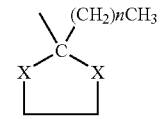

where each X is independently selected from CH$_2$, O, S and NH and n is an integer from 3-5;

if Y is C=O, and R$_1$ is selected from H, OH, OCH$_3$, NH$_2$, O(CH$_2$)$_n$N(CH$_3$)$_2$ (where n is an integer from 1-3) or

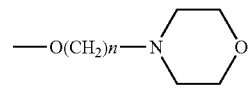

(where n is an integer between 1-3), and R$_2$ is selected from H, OH or OCH$_3$, then R$_3$ cannot be selected from structure Ia 3 where D is an adamantyl ring and R$_4$ is selected from H, (CH$_2$)$_n$CH$_3$ (where n is an integer from 4-6) or C(CH$_3$)$_2$(CH$_2$)$_n$CH$_3$ (where n is an integer from 3-5);

if Y is C=O, and R$_1$ and R$_2$ are both OH, then R$_3$ cannot be structure Ia 3, where D is a 5 to 8 membered unsubstituted cycloalkyl ring or 5 to 8 membered unsubstituted cycloalkenyl ring and R$_4$ is H;

if Y is C=O, and R$_1$ and R$_2$ are both OH, then R$_3$ cannot be structure Ia 5, where R$_6$ and R$_7$ are both H and R$_8$ is (CH$_2$)$_j$—C(R$_6$)=C(R$_7$)—(CH$_2$)$_k$—R$_5$ where R$_5$ is H and the sum of j and k is equal to 4-9; and if Y is C=O, and R$_1$ and R$_2$ are both OH, then R$_3$ cannot be CH=CH(CH$_2$)$_n$CH$_3$ where n is an integer from 2-7.

2. A compound of claim 1 wherein:
Y is >C=O;
R$_1$ and R$_2$ are each OH; and
R$_3$ is selected from

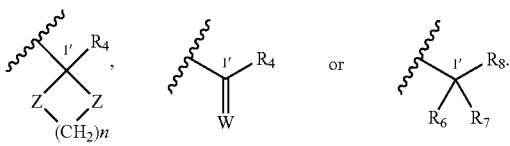

3. A compound of claim 1 wherein:
Y is >C=O;
$R_1$ and $R_2$ are each OH;
$R_3$ is

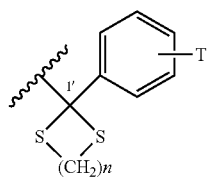

T is selected from alkyl, alkyl substituted with one or more groups selected from halogen, OH, CN, sulfonamide, NCS or $NO_2$; alkenyl, alkenyl substituted with one or more groups selected from halogen, OH, CN, sulfonamide, NCS or $NO_2$; alkynyl or alkynyl substituted with one or more groups selected from halogen, OH, CN, sulfonamide, NCS or $NO_2$; and
n is an integer 0 to 3.

4. A compound of claim 1 wherein:
Y is >C=O;
$R_1$ and $R_2$ are each OH;
$R_3$ is

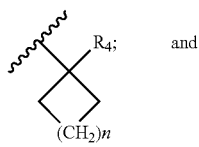

n is an integer 0 to 3.

5. A compound of claim 1 wherein:
Y is >C=O;
$R_1$ and $R_2$ are each OH;
$R_3$ is

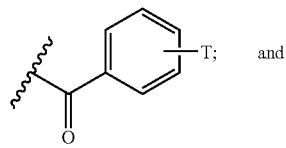

T is selected from alkyl, alkyl substituted with one or more groups selected from halogen, OH, CN, sulfonamide, NCS or $NO_2$; alkenyl, alkenyl substituted with one or more groups selected from halogen, OH, CN, sulfonamide, NCS or $NO_2$; alkynyl or alkynyl substituted with one or more groups selected from halogen, OH, CN, sulfonamide, NCS or $NO_2$.

6. A pharmaceutical composition containing a therapeutically effective amount of at least one of the compounds of claim 1.

7. A method of stimulating cannabinoid receptors in an individual or animal comprising administering to the individual or animal a therapeutically effective amount of at least one of the compounds of claim 1 in purified form.

8. The method of claim 7 wherein the compound more selectively binds to the CB2 cannabinoid receptors in the individual or animal.

9. A compound of formula Ia below, including physiologically acceptable salts, diastereomers, enantiomers, double bond isomers, or mixtures thereof;

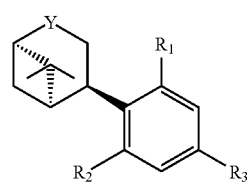

Ia wherein:
Y is selected from >C=O or >C=$CY_7Y_8$, including all isomers,
$Y_7$ and $Y_8$ are each independently selected from H, alkyl, alkenyl, CN, OH, alkoxy or —$(CH_2)_n$—$NR_{10}R_{11}$,
$R_{10}$ and $R_{11}$ are each independently selected from H, alkyl, hydroxyalkyl, or $R_{10}$ and $R_{11}$ together comprise part of a 3 to 7 membered saturated heterocyclic ring containing up to one additional heteroatom selected from N, O and S,
n is an integer from 0 to about 4, wherein when an integer is 0 the structural portion modified by that integer is absent and the adjacent subunits are directly connected;
$R_1$ and $R_2$ are each independently selected from H, OH, $NH_2$, $NO_2$, CN, $OCOCH_3$, OC(O)CH=CHCOOH, halogen, alkyl, —O-alkyl, acyl, aroyl, benzoyl, substituted benzoyl, phenacyl, substituted phenacyl, —O-alkyl-aryl, —O-alkyl-$NR_{10}R_{11}$, —O-alkyl-COOR (where R is selected from H or alkyl), —O-alkyl-$CONR_{10}R_{11}$, —$N(alkyl)_2$, —CO(alkyl)X or —OCO(alkyl)X or OCO(alkenyl)X(where X is selected from H, COOH, dialkylamino, a cyclic amine, a carbocyclic ring, a heterocyclic ring, an aromatic ring or a heteroaromatic ring), —O—P(O)$(OR)_2$ or —O—P(O)(OH)(OR) (where R is selected from H or alkyl), —P(O)$(OR)_2$ (where R is selected from H or alkyl), —P(O)(OH)(OR) (where R is selected from H or alkyl) or —OC(O)—CH($NH_2$)—$R_{16}$ (where $R_{16}$ is selected from H, CH(OH)$CH_3$ or alkyl-$X_3$ and $X_3$ is selected from: H, —NH—C(=NH)$NH_2$, C(O)$NH_2$, COOH, SH, $SCH_3$, OH, $NH_2$, a substituted or unsubstituted aromatic ring, a substituted or unsubstituted heteroaromatic ring, a substituted or unsubstituted heterocyclic ring,
$R_{10}$ and $R_{11}$ are each independently selected from H, alkyl, hydroxyalkyl or $R_{10}$ and $R_{11}$ together comprise part of a 3 to 7 membered saturated heterocyclic ring containing up to one additional heteroatom selected from N, O and S; and $R_3$ is

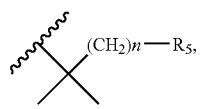

wherein $R_5$ is selected from H, halogen, CN, $CF_3$, $N_3$, COOH, $NH_2$, $N(CH_3)_2$, $\oplus N(CH_3)_3$, $Sn(alkyl)_3$, phenyl, OH, NCS, NCO, $NO_2$, CHO, $SO_3H$, $SO_2Cl$, $SO_2F$, $PO_3H_2$, $C(O)CF_3$, SH, —CH=$CH_2$, —C≡CH, NH(alkyl), N(alkyl)$_2$, O-aryl, alkoxy, thioalkoxy, sulfonamide, COOR (where R is selected from H or alkyl), a substituted or unsubstituted carbocyclic ring, a substituted or unsubstituted heterocyclic ring, a substituted or unsubstituted aromatic ring, a substituted or unsubstituted heteroaromatic ring, a polycarbocyclic ring structure having 2 to about 5 rings, a polyheterocyclic ring structure having 2 to about 5 rings or $CONR_{10}R_{11}$ (where $R_{10}$ and $R_{11}$ are each independently selected from H, alkyl, hydroxyalkyl, or $R_{10}$ and $R_{11}$ together comprise part of a 5 or 6 membered saturated heterocyclic ring containing up to one additional heteroatom selected from N, O and S), n is an integer from 0 to about 7, wherein when an integer is 0 the structural portion modified by that integer is absent and the adjacent subunits are directly connected;

with the following provisos:
if Y is C=O, and $R_1$ and $R_2$ are both OH, then $R_3$ cannot be $C(CH_3)_2(CH_2)_nCH_3$ (where n is an integer from 3-5).

10. A pharmaceutical composition containing a therapeutically effective amount of at least one of the compounds of claim 9.

11. A method of stimulating cannabinoid receptors in an individual or animal comprising administering to the individual or animal a therapeutically effective amount of at least one of the compounds of claim 9 in purified form.

12. The method of claim 11 wherein the compound more selectively binds to the CB2 cannabinoid receptors in the individual or animal.

13. A compound of formula Ib below, including physiologically acceptable salts, diastereomers, enantiomers, double bond isomers, or mixtures thereof;

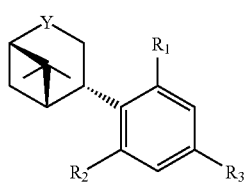

Ib wherein:
Y is selected from >C=O, >CH—$(CH_2)_f$—$Y_1$—$(CH_2)_g$—$Y_2$, >C=N—$Y_3$, >CH—$NY_4Y_5$ or >CH—$(CH_2)_h$—$Y_6$, including all isomers, $Y_1$ is independently selected from O, C(O)O or $CH_2$, $Y_2$ is independently selected from H, I, CN, $CF_3$, $N_3$, NCS or NCO, $Y_3$ is independently selected from OH, $NH_2$, C1-C4 alkoxy, C1-C4 alkyl, —$(CH_2)_n$—$NR_{10}R_{11}$, —$(CH_2)_n$—$CO_2R$ (where R comprises H or alkyl), —O—$(CH_2)_n$—$NR_{10}R_{11}$, —O—$(CH_2)_n$—$CO_2R$ (where R comprises H or alkyl) or —O—$(CH_2)_n$—$CONR_{10}R_{11}$, $Y_4$ is independently selected from H, OH, C1-C4 alkoxy or C1-C4 alkyl, $Y_5$ is independently selected from H, OH, C1-C4 alkoxy or C1-C4 alkyl, wherein $Y_4$ and $Y_5$ cannot both be OH and wherein $Y_4$ and $Y_5$ cannot both be C1-C4 alkoxy, $Y_6$ is independently selected from I, CN, $SO_2Cl$, $SO_2F$, COalkyl, $CF_3$, COfluoroalkyl, $N_3$, NCS or NCO, $R_{10}$ and $R_{11}$ are each independently selected from hydroxyalkyl, or $R_{10}$ and $R_{11}$ together comprise part of a 3 to 7 membered saturated heterocyclic ring containing one additional heteroatom selected from N, O and S, f comprises an integer from 0 to about 5, g comprises an integer from 0 to about 5, h comprises an integer from 0 to about 5, n comprises an integer from 0 to about 4, wherein when an integer is 0 the structural portion modified by that integer is absent and the adjacent subunits are directly connected, $R_1$ and $R_2$ are each independently selected from OH, $OCH_3$, $NO_2$, CN, $OCOCH_3$, aroyl, benzoyl, substituted benzoyl, phenacyl, substituted phenacyl, —O-alkylaryl, —O-alkyl-$NR_{10}R_{11}$, —O-alkyl-$CONR_{10}R_{11}$, —CO(alkyl)X or —OCO(alkyl)X (where X is selected from a cyclic amine, a carbocyclic ring, a heterocyclic ring, an aromatic ring or a heteroaromatic ring), —OC(O)—CH($NH_2$)—R (where R comprises H or CH(OH)$CH_3$) or alkyl-X (where X is selected from H, —NH—C(=NH)$NH_2$, C(O)$NH_2$, COOH, SH, $SCH_3$, OH, $NH_2$, a substituted or unsubstituted aromatic ring, a substituted or unsubstituted heteroaromatic ring, a substituted or unsubstituted heterocyclic ring), $R_{10}$ and $R_{11}$ are each independently selected from hydroxyalkyl, or $R_{10}$ and $R_{11}$ together comprise part of a 3 to 7 membered saturated heterocyclic ring containing one additional heteroatom selected from N, O and S; and $R_3$ is selected from the following structures:

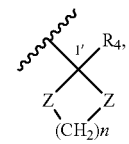

Ib 1

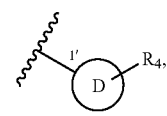

Ib 2

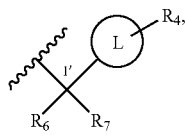

Ib 3

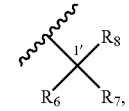

Ib 4

-continued

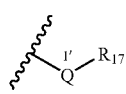

Ib 5 wherein each Z is independently selected from $CH_2$, S, O, NH, $N(CH_3)$, SO or $SO_2$, D is selected from a heterocyclic ring, an adamantyl ring, an heteroadamantyl ring or any above ring optionally substituted by $R_4$ in any possible position with the proviso that ring D can not be bonded to $R_4$ from the 1' position, L is selected from a cycloalkyl ring, a heterocyclic ring, a heteroaromatic ring, an adamantyl ring, a heteroadamantyl ring or any above ring optionally substituted by $R_4$ in any possible position, $R_4$ is —$(CH_2)_j$-A-$(CH_2)_k$—$R_5$, A is selected from —$CH_2$—$CH_2$—, —CH=CH—, —C≡C—, O, S, SO, $SO_2$ or NH, $R_5$ is selected from H, halogen, CN, $CF_3$, $N_3$, COOH, $NH_2$, $N(CH_3)_2$, $\oplus N(CH_3)_3$, $Sn(alkyl)_3$, phenyl, pyrrolidine ring, piperidine ring, morpholine ring, cyclopropyl, cyclobutyl, cyclopentyl, cyclohexyl, cycloheptyl, NCS, NCO, $SO_3H$, $SO_2Cl$, $SO_2F$, $PO_3H_2$, $C(O)CF_3$, —O-aryl, sulfonamide, a carbocyclic ring, a heterocyclic ring, a heteroaromatic ring, a polycarbocyclic ring structure having 2 to about 5 rings, a polyheterocyclic ring structure having 2 to about 5 rings or $CONR_{10}R_{11}$ (where $R_{10}$ and $R_{11}$ are each independently selected from hydroxyalkyl, or $R_{10}$ and $R_{11}$ together comprise part of a 5 or 6 membered saturated heterocyclic ring containing one additional heteroatom selected from N, O and S), n is an integer from 0 to about 3, j is an integer from 0 to about 7, k is an integer from 0 to about 7, wherein when an integer is 0 the structural portion modified by that integer is absent and the adjacent subunits are directly connected, $R_6$ and $R_7$ are each independently selected from H or $CH_3$, $R_8$ is selected from —$(CH_2)_j$—C≡C—$(CH_2)_k$—$R_5$ or —$(CH_2)_j$—CH=CH—$(CH_2)_k$—$R_5$, $R_5$ is selected from H, halogen, CN, $CF_3$, $N_3$, COOH, $NH_2$, $N(CH_3)_2$, $\oplus N(CH_3)_3$, $Sn(alkyl)_3$, phenyl, pyrrolidine ring, piperidine ring, morpholine ring, cyclopropyl, cyclobutyl, cyclopentyl, cyclohexyl, cycloheptyl, NCS, NCO, $SO_3H$, $SO_2Cl$, $SO_2F$, $PO_3H_2$, $C(O)CF_3$, —O-aryl, sulfonamide, a carbocyclic ring, a heterocyclic ring, a heteroaromatic ring, a polycarbocyclic ring structure having 2 to about 5 rings, a polyheterocyclic ring structure having 2 to about 5 rings or $CONR_{10}R_{11}$ (where $R_{10}$ and $R_{11}$ are each independently selected from hydroxyalkyl, or $R_{10}$ and $R_{11}$ together comprise part of a 5 or 6 membered saturated heterocyclic ring containing one additional heteroatom selected from N, O and S), j is an integer from 0 to about 7, k is an integer from 0 to about 7, wherein when an integer is 0 the structural portion modified by that integer is absent and the adjacent subunits are directly connected, Q is selected from O, S, NH or $N(R_{18})$ (where $R_{18}$ is selected from $SO_2$-aryl, alkyl-$R_5$, aryl-$R_5$ or heteroaryl-$R_5$), $R_{17}$ is selected from alkyl-$R_5$, aryl-$R_5$ or heteroaryl-$R_5$ with the proviso that $R_5$ cannot be hydrogen;

with the following proviso:

if Y is C=O, and $R_1$ and $R_2$ are both OH, then $R_3$ cannot be structure Ib 4, where $R_6$ and $R_7$ are both H and $R_8$ is $(CH_2)_j$—CH=CH—$(CH_2)_k$—$R_5$ where R5 is H and the sum of j and k is equal to 4-9.

14. A pharmaceutical composition containing a therapeutically effective amount of at least one of the compounds of claim 13.

15. A method of stimulating cannabinoid receptors in an individual or animal comprising administering to the individual or animal a therapeutically effective amount of at least one of the compounds of claim 13 in purified form.

16. The method of claim 15 wherein the compound more selectively binds to the CB2 Cannabinoid receptors in the individual or animal.

* * * * *